(12) United States Patent
Mascharak et al.

(10) Patent No.: US 12,236,599 B2
(45) Date of Patent: Feb. 25, 2025

(54) SYSTEMS AND METHODS FOR ANALYZING, DETECTING, AND TREATING FIBROTIC CONNECTIVE TISSUE NETWORK FORMATION

(71) Applicant: The Board of Trustees of the Leland Stanford Junior University, Stanford, CA (US)

(72) Inventors: Shamik Mascharak, Santa Cruz, CA (US); Heather E. Talbott, Portola Valley, CA (US); Mimi Borrelli, Stanford, CA (US); Alessandra Laura Moore, Stanford, CA (US); Michael T. Longaker, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 383 days.

(21) Appl. No.: 17/597,833

(22) PCT Filed: Jul. 27, 2020

(86) PCT No.: PCT/US2020/043717
§ 371 (c)(1),
(2) Date: Jan. 25, 2022

(87) PCT Pub. No.: WO2021/021720
PCT Pub. Date: Feb. 4, 2021

(65) Prior Publication Data
US 2022/0261996 A1 Aug. 18, 2022

Related U.S. Application Data

(60) Provisional application No. 62/879,366, filed on Jul. 26, 2019.

(51) Int. Cl.
*G06T 7/00* (2017.01)
*G06T 5/70* (2024.01)
(Continued)

(52) U.S. Cl.
CPC .............. *G06T 7/0014* (2013.01); *G06T 5/70* (2024.01); *G06T 7/13* (2017.01); *G06T 7/90* (2017.01);
(Continued)

(58) Field of Classification Search
CPC .......... G06T 7/0014; G06T 7/13; G06T 7/90; G06T 5/70; G06T 2207/10024;
(Continued)

(56) References Cited

U.S. PATENT DOCUMENTS

2003/0154032 A1* 8/2003 Pittman .............. C07K 14/4713
702/20
2010/0111398 A1* 5/2010 Mitra ........................ G06T 7/12
382/133
(Continued)

FOREIGN PATENT DOCUMENTS

BR 1120220014465 A2 7/2022
CN 105009174 A 10/2015
(Continued)

OTHER PUBLICATIONS

Extended European Search Report for European Application No. 20846594.8, Search completed Jul. 17, 2023, Mailed Jul. 25, 2023, 12 pgs.
(Continued)

*Primary Examiner* — Michael R Neff
(74) *Attorney, Agent, or Firm* — KPPB LLP

(57) ABSTRACT

A system and method for analyzing a plurality of tissue image samples at different stages of image processing in order to establish the level of fibrosis within a patient from
(Continued)

which the tissue image sample was retrieved. Various embodiments incorporate machine learning techniques which enable an automated progressive approach to effectively and efficiently diagnosing fibrotic conditions based on tissue image samples.

17 Claims, 29 Drawing Sheets

(51) Int. Cl.
  *G06T 7/13* (2017.01)
  *G06T 7/90* (2017.01)
  *A61B 5/00* (2006.01)

(52) U.S. Cl.
  CPC ..... *A61B 5/444* (2013.01); *G06T 2207/10024* (2013.01); *G06T 2207/20084* (2013.01); *G06T 2207/30004* (2013.01)

(58) Field of Classification Search
  CPC . G06T 2207/20084; G06T 2207/30004; A61B 5/444
  USPC ......................................................... 382/128
  See application file for complete search history.

(56) References Cited

U.S. PATENT DOCUMENTS

| | | | |
|---|---|---|---|
| 2013/0030305 | A1 | 1/2013 | Yu et al. |
| 2015/0339816 | A1 | 11/2015 | Yu et al. |
| 2016/0012583 | A1 | 1/2016 | Cales et al. |
| 2016/0110632 | A1* | 4/2016 | Kiraly ................. G06T 7/11 382/128 |
| 2019/0164642 | A1* | 5/2019 | Hartung ................ G06V 10/82 |
| 2020/0378991 | A1* | 12/2020 | Jia .............................. A61P 1/16 |
| 2022/0298234 | A1* | 9/2022 | Elisseeff ................ A61K 38/20 |

FOREIGN PATENT DOCUMENTS

| | | |
|---|---|---|
| CN | 107818821 A | 3/2018 |
| CN | 109994199 A | 7/2019 |
| CN | 114340500 A | 4/2022 |
| EP | 4003173 A1 | 6/2022 |
| HK | 40068388 A | 9/2022 |
| JP | 2021500691 A | 1/2021 |
| JP | 2022542150 A | 9/2022 |
| WO | 2018216280 A1 | 11/2018 |
| WO | 2019005847 A1 | 1/2019 |
| WO | 2019077108 A2 | 4/2019 |
| WO | 2021021720 A1 | 2/2021 |

OTHER PUBLICATIONS

International Preliminary Report on Patentability for International Application PCT/US2020/043717, Report issued Feb. 1, 2022, Mailed on Feb. 10, 2022, 6 pgs.
International Search Report and Written Opinion for International Application No. PCT/US2020/043717, Search completed Oct. 12, 2020, Mailed Oct. 27, 2020, 10 pgs.
Bartholmai et al., "Quantitative Computed Tomography Imaging of Interstitial Lung Disease", Journal of Thoracic Imaging, vol. 28, No. 5, Sep. 2013, pp. 298-307, doi: 10.1097/RTI.0b013e3182a21969.
Bayat et al., "Clinical Management of Skin Scarring", Skinmed, vol. 4, No. 3, May-Jun. 2005, pp. 165-173, doi: 10.1111/j.1540-9740. 2005.02507.x.
Bayat et al., "Skin scarring", BMJ, vol. 326, No. 7380, Jan. 11, 2003, pp. 88-92, doi: 10.1136/bmj.326.7380.88.
Bredfeldt et al., "Automated quantification of aligned collagen for human breast carcinoma prognosis", Journal of Pathology Informatics, vol. 5, No. 28, 13 pgs., Published online Aug. 28, 2014, doi: 10.4103/2153-3539.139707.
Chinta et al., "Abstract 37: Machine Learning Analysis of Connective Tissue Networks Enables Objective Characterization of Skin Fibroses", Plastic and Reconstructive Surgery Global Open, vol. 7, No. 4 Suppl, Apr. 1, 2019, pp. 27-28, XP093063814, doi: 10.1097/01.GOX.0000558311.64337.ba.
Claman et al., "Endothelial and Fibroblastic Activation in Scleroderma, The Myth of the Uninvolved Skin", Arthritis & Rheumatism, vol. 34, No. 12, 1991, pp. 1495-1501, doi: 10.1002/art.1780341204.
Clements et al., "Inter and Intraobserver Variability of Total Skin Thickness Score (Modified Rodnan TSS) in Systemic Sclerosis", Journal of Rheumatology, vol. 22, 1995, pp. 1281-1285.
Crowley et al., "Automated detection of heuristics and biases among pathologists in a computer-based system", Advances in Health Sciences Education: Theory and Practice, vol. 18, No. 3, 2013, pp. 343-363, doi: 10.1007/s10459-012-9374-z.
Czirjak et al., "The EUSTAR model for teaching and implementing the modified Rodnan skin score in systemic sclerosis", The Annals of the Rheumatic Diseases, vol. 66, No. 7, 2007, pp. 966-969, doi: 10.1136/ard.2006.066530.
Esteva et al., "Dermatologist-level classification of skin cancer with deep neural networks", Nature, vol. 542, No. 7639, Feb. 2, 2017, pp. 115-118, published online Jan. 25, 2017, doi:10.1038/nature21056.
Eva et al., "Heuristics and biases—a biased perspective on clinical reasoning", Medical Education, vol. 39, Sep. 3, 2005, pp. 870-872, doi: 10.1111/j.1365-2929.2005.02258.x.
Fearmonti et al., "A Review of Scar Scales and Scar Measuring Devices", Eplasty, vol. 10, e43, 2010, pp. 1-13, published online Jun. 21, 2010.
Galiano et al., "Quantitative and reproducible murine model of excisional wound healing", Wound Repair and Regeneration, vol. 12, No. 4, Jul. 19, 2004, pp. 485-492, doi: 10.1111/j.1067-1927. 2004.12404.x.
Gianelli et al., "The European Consensus on grading of bone marrow fibrosis allows a better prognostication of patients with primary myelofibrosis", Modern Pathology, vol. 25, No. 9, May 25, 2012, pp. 1193-1202, doi: 10.1038/modpathol.2012.87.
Goodman, "Grading and staging systems for inflammation and fibrosis in chronic liver diseases", Journal of Hepatology, vol. 47, No. 4, 2007, pp. 598-607, doi: 10.1016/j.jhep.2007.07.006.
Gressner et al., "Biomarkers of liver fibrosis: Clinical translation of molecular pathogenesis or based on liver-dependent malfunction tests", Clinica Chimica Acta, vol. 381, No. 2, Jun. 2007, pp. 107-113, doi: 10.1016/j.cca.2007.02.038.
Guglielmelli et al., "MIPSS70: Mutation-Enhanced International Prognostic Score System for Transplantation-Age Patients with Primary Myelofibrosis", Journal of Clinical Oncology, vol. 36, No. 4, Feb. 1, 2018, pp. 310-318, doi: 10.1200/jco.2017.76.4886.
Gurtner et al., "Wound repair and regeneration", Insight Review, vol. 453, No. 7193, May 15, 2008, pp. 314-321, doi: 10.1038/nature07039.
Huang et al., "A methodology for exploring biomarker—phenotype associations: application to flow cytometry data and systemic sclerosis clinical manifestations", BMC Bioinformatics, vol. 16, No. 293, 2015, pp. 1-15, doi: 10.1186/s12859-015-0722-x.
Jordan et al., "Performance of the new ACR/EULAR classification criteria for systemic sclerosis in clinical practice", Rheumatology (Oxford), vol. 54, No. 8, Aug. 2015, pp. 1454-1458, doi: 10.1093/rheumatology/keu530.
Junqueira et al., "Differential Staining of Collagens Type I, II and III by Sirius Red and Polarization Microscopy", Archivum histologicum japonicum, vol. 41, No. 3, 1978, pp. 267-274, doi: 10.1679/aohc1950. 41.267.
Junqueira et al., "Picrosirius staining plus polarization microscopy, a specific method for collagen detection in tissue sections", Histochemical Journal, 1979, vol. 11, No. 4, pp. 447-455, doi: 10.1007/BF01002772.
Khanna et al., "Standardization of the modified Rodnan skin score for use in clinical trials of systemic sclerosis", Journal of Scleroderma and Related Disorders, vol. 2, No. 1, Feb. 2, 2017, pp. 11-18.
Kowal-Bielecka et al., "Update of EULAR recommendations for the treatment of systemic sclerosis", Annals of the Rheumatic Diseases, vol. 76, No. 8, 2017, pp. 1327-1339, doi: 10.1136/annrheumdis-2016-209909.

(56) References Cited

OTHER PUBLICATIONS

Lee et al., "Histopathological Differential Diagnosis of Keloid and Hypertrophic Scar", American Journal of Dermatopathology, vol. 26, No. 5, Oct. 2004, pp. 379-384, doi: 10.1097/00000372-200410000-00006.

Liu et al., "Methods for Quantifying Fibrillar Collagen Alignment", Methods in Molecular Biology, vol. 1627, 2017, pp. 429-451, doi: 10.1007/978-1-4939-7113-8_28.

Matalka et al., "Quantitative assessment of liver fibrosis: a novel automated image analysis method", Liver International, vol. 26, No. 9, Nov. 1, 2006, pp. 1054-1064, XP093064038, doi: 10.1111/j.1478-3231.2006.01341.x.

Mendoza et al., "Systemic Sclerosis Disease Modification Clinical Trials Design: Quo Vadis?", Arthritis Care & Research (Hoboken), vol. 64, No. 7, Jul. 2012, pp. 945-954, doi: 10.1002/acr.21667.

Pandol et al., "Desmoplasia of Pancreatic Ductal Adenocarcinoma", Clinical Gastroenterology and Hepatology, vol. 7, No. 11, Nov. 2009, pp. S44-S47, doi: 10.1016/j.cgh.2009.07.039.

Rinkevich et al., "Identification and isolation of a dermal lineage with intrinsic fibrogenic potential", Science, vol. 348, No. 6232, Apr. 17, 2015, pp. aaa2151-aaa2151-14, doi: 10.1126/science.aaa2151.

Ruifrok et al., "Quantification of Histochemical Staining by Color Deconvolution", Analytical and Quantitative Cytology and Histology, vol. 23, No. 4, Aug. 2001, pp. 291-299.

Saposnik et al., "Cognitive biases associated with medical decisions: a systematic review", BMC Medical Informatics and Decision Making, vol. 16, No. 138, Nov. 3, 2016, 14 pgs., doi: 10.1186/s12911-016-0377-1.

Sen et al., "Human skin wounds: A major and snowballing threat to public health and the economy", Wound Repair Regeneration, vol. 17, No. 6, 2009, pp. 763-771, doi: 10.1111/j.1524-475x.2009.00543.x.

Sennett et al., "A scar is born: Origins of fibrotic skin tissue", Science, vol. 348, No. 6232, Apr. 17, 2015, pp. 284-285, doi: 10.1126/science.aab0120.

Taroni et al., "A novel multi-network approach reveals tissue-specific cellular modulators of fibrosis in systemic sclerosis", Genome Medicine, vol. 9, No. 27, 2017, 24 pgs., doi: 10.1186/s13073-017-0417-1.

Tversky et al., "Judgment under Uncertainty: Heuristics and Biases", Science, vol. 185, No. 4157, Sep. 27, 1974, pp. 1124-1131, doi: 10.1126/science.185.4157.1124.

Van Den Hoogen, "2013 Classification Criteria for Systemic Sclerosis: An American College of Rheumatology/European League Against Rheumatism Collaborative Initiative", Annals of the Rheumatic Diseases, vol. 72, No. 11, 2013, pp. 1747-1755, doi: 10.1136/annrheumdis-2013-204424.

Van Praet et al., "Histopathological cutaneous alterations in systemic sclerosis: a clinicopathological study", Arthritis Research & Therapy, vol. 13, No. 1, Article No. R35, Feb. 28, 2011, pp. 1-7, doi:10.1186/ar3267.

Walker, "The complexities of breast cancer desmoplasia", Breast Cancer Research, vol. 3, No. 3, Feb. 1, 2001, pp. 143-145, doi: /10.1186/bcr287.

Wynn, "Cellular and molecular mechanisms of fibrosis", Journal of Pathology, vol. 214, No. 2, Jan. 2008, pp. 199-210, doi:10.1002/path.2277.

Wynn, "Fibrotic Disease and the TH1/TH2 Paradigm", Nature Reviews Immunology, vol. 4, No. 8, Aug. 2004, pp. 583-594, doi: 10.1038/nri1412.

Yu et al., "Deep learning enables automated scoring of liver fibrosis stages", Scientific Reports, vol. 8, No. 1, Oct. 30, 2018, 10 pgs., XP055682455, doi: 10.1038/s41598-018-34300-2.

\* cited by examiner

| Parameter | Description |
|---|---|
| Brightness | Grayscale intensity (0-255) of the image |
| Number of Fibers | Number of objects detected, scaled, and reported as fibers per 1000 microns. |
| Length | Length of binary objects, measured as major axis length in pixels and scaled and reported in microns. |
| Width | Width of binary objects, measured as minor axis length in pixels and scaled and reported in microns |
| Persistence | Pixel length of binary objects divided by pixel distance between their ends |
| Alignment | Quantified angles of orientation (0-360 degrees) for each fiber fit to the von Mises distribution to derive the k value. As reported (K), higher values indicate greater fiber alignment. |
| Number of Branchpoints | Number of branchpoints detected in the skeletonized fibre map, scaled and reported as branchpoints per 1000 microns |
| Euler Number | Number of objects detected minus the number of holes within each object. Lower values indicate a porous fiber network. |
| Extent | Ratio of pixels in the image to pixels in the smallest box containing all objects. |
| Perimeter | Pixel length around the boundary of each object, scaled and reported in microns |
| Solidity | Proportion of pixels in the convex hull, the smallest convex region containing all detected objects. |
| Eccentricity | Ratio of the distance between foci of an ellipse with the same second moment as the image. |
| Equivalent Diameter | Diameter of a circle with the same area as detected objects. |

| Parameter | Explanation |
|---|---|
| Area | Fiber area |
| Major Axis Length | Length of fiber's long axis |
| Minor Axis Length | Length of fiber's short axis |
| Eccentricity | Ratio of long:short axis length |
| Convex Area | Area of a convex hull fit to fiber |
| Circularity | Roundness of fiber |
| Filled Area | Area of a bounding box fit to fiber |
| Max Intensity | Maximum pixel intensity of fibers |
| Min Intensity | Minimum pixel intensity of fibers |
| Mean Intensity | Average pixel intensity of fibers |
| Max Feret Diameter | Maximum distance between any two boundary points on the antipodal vertices of convex hulls around each fiber |
| Min Feret Diameter | Minimum distance between any two boundary points on the antipodal vertices of convex hulls around each fiber |
| Max Feret Angle | Angle between the maximum Feret diameter and the horizontal axis of the image |
| Min Feret Angle | Angle between the minimum Feret diameter and the horizontal axis of the image |
| Median Alpha | Median fiber alignment |
| Skewness Alpha | Skewness of fiber alignment |
| Kappa | Average coefficient of alignment |
| Contrast | Intensity contrast between pixels and their neighbors across the image |
| Correlation | Intensity correlation between pixels and their neighbors across the image |
| Energy | Sum of the squared elements of a gray-level co-occurrence matrix (GLCM) |
| Homogeneity | Closeness of the distribution of elements in the GLCM to the GLCM diagonal |
| Branchpoint Density | Quantification of fiber branchpoints from the skeletonized image |

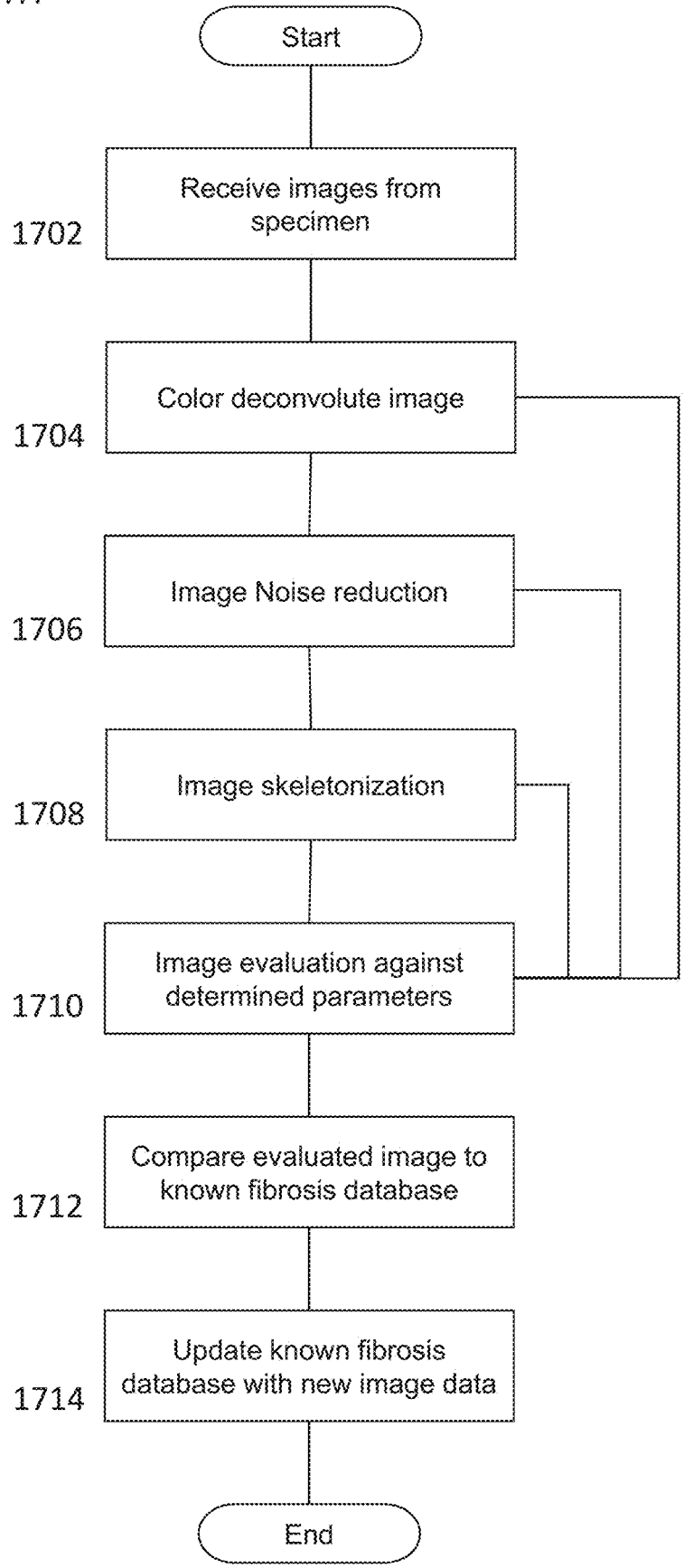

SYSTEMS AND METHODS FOR ANALYZING, DETECTING, AND TREATING FIBROTIC CONNECTIVE TISSUE NETWORK FORMATION

CROSS-REFERENCED APPLICATIONS

This application is a national stage of PCT Application No. PCT/US20/43717 filed on Jul. 27, 2020, which application claims priority to U.S. Provisional application 62/879,366 filed on Jul. 26, 2019, the disclosures of which are included herein by reference in their entireties.

STATEMENT OF FEDERAL FUNDING

The invention described herein was made with government support under contracts R01-GM116892 and U24-DE026914 awarded by the National Institutes of Health. The Government has certain rights in the invention.

FIELD OF THE INVENTION

The present invention generally relates to the analysis and detection of tissue network formation. More specifically, the systems and methods used to analyze and detect fibrosis formation within tissue.

BACKGROUND OF THE INVENTION

Fibrosis, or deposition of excess connective tissue, represents a major cause of morbidity worldwide. It is estimated that 45% of deaths in the United States are attributable to major-organ fibrosis (e.g., myocardial infarct, stroke, liver cirrhosis), fibroproliferative disorders (e.g., scleroderma, myelofibrosis), and scarring associated with trauma. In some instances, fibrosis can occur idiopathically without any known cause, while in other instances it can occur after injury to some tissue such as in the lungs, the liver, the peritoneum, the skin, and/or other organs. For example, a minimum of 100 million patients per year in the developed world acquire scars as a result of surgical procedures, trauma, and burns. These healed wounds can have functional, social, and psychological consequences, particularly hypertrophic scars and keloids. Additionally, fibrosis and the resulting consequences have been responsible for more than $20 billion annually in health care costs in the United States alone. Furthermore, any misdiagnosis or mismanagement of fibroses can impose further medical and financial burden on patients.

Histopathology is the study of a diagnosis of tissues diseases that often involves the evaluation of tissues under at a microscopic level. Typical specimens are often evaluated using staining techniques such as Masson's Trichrome, Picrosirius Red, collagen immunostaining, Reticulin silver. Histopathological evaluations of specimens processed with connective tissue stains are integral to the clinical management of fibrotic diseases. These modalities are used to assess disease status, monitor treatment response, and evaluate effects of new therapies in the research pipeline. Histopathological evaluation also governs clinical decision-making; for example, myelofibrosis grading using the myelofibrosis (MF) scale informs eligibility for curative hematopoietic stem cell transplant. In contrast to other prevalent diseases such as cancer (for which objective, minimally invasive methods for assessing disease burden exist), current practice for evaluating fibroses relies on qualitative scoring of gross or biopsied tissue. These analyses, even when performed by trained pathologists, are inherently reliant on user observation of the cells and connective tissue matrix to select "representative" images and estimate scores on a visual analogue scale. Visual assessment, even by trained pathologists, is inherently subjective, time consuming, and bias-prone. Thus, existing methods may fail to accurately represent disease status or to capture subtle yet clinically significant changes in disease progression. Resulting misdiagnosis or mismanagement of fibroses can increase medical and financial burden on patients.

SUMMARY OF THE INVENTION

Many embodiments are directed to a method for tissue analysis utilizes the following steps:
  obtaining at least one tissue sample image from a patient;
  processing the at least one tissue sample image such that a fiber network can be identified and quantified within the at least one tissue sample image;
  evaluating the processed sample image against a set of parameters wherein the set of parameters correspond to fiber characteristics, wherein the set of parameter are quantified from the at least one sample image and wherein the quantified parameters are weighted against a known set of fiber characteristics for establishing a level of fibrosis within the at least one sample image; and
  assigning a fibrotic tissue classification to the at least one sample image.

In other embodiments, the method has a plurality of sample images, wherein the plurality of sample images are representative of a number of different potential diseases.

In still other embodiments, the set of predetermined parameters are selected from a group consisting of length, width, and number of fibers, brightness, persistence, and alignment, number of branch points, Euler number, perimeter, solidity, eccentricity, and equivalent diameter.

In yet other embodiments, the processing further comprises color deconvolution of the at least one image.

In still yet other embodiments, the processing further comprises image noise reduction In other embodiments, the image noise reduction is done by adaptive edge preserving.

In still other embodiments, the processing further comprises image binarization.

In yet other embodiments, the processing further comprises color deconvolution, noise reduction, and binarization.

In still yet other embodiments, the evaluating is completed using a neural network system having an input layer, a hidden layer, and an output layer.

In other embodiments, the neural network system of is an unsupervised neural network.

In still other embodiments, the neural network system is a supervised neural network.

In yet other embodiments, wherein the neural network system has a plurality of hidden layers.

In still yet other embodiments, the method further produces a data set of evaluated and assigned images wherein the data set is used for new set of input images.

In other embodiments, the method further develops a treatment plan for a patient based on the assigned tissue classification.

In still other embodiments, further treats a patient from which the sample image was obtained based on the developed treatment plan in accordance with the assigned tissue classification.

In yet other embodiments, further utilizes the assigned tissue classification to update a database of tissue parameters by which a subsequent set of tissue image samples can be analyzed.

Other embodiments include a system for analyzing tissue sample images that has a processor configured to receive a set of input images and process the images in order to reduce them to a simplified image of tissue connection networks. Additionally the system has a memory storage device comprising at least a trained neural network program and a predetermined set of parameters, and wherein the processor uses the trained neural network and predetermined set of parameters to analyze the simplified image. The system may also have an output device configured to receive the analyzed image and assign a disease category a severity level.

In various embodiments the system may be used to establish and utilize a treatment plan for a patient with the assigned disease category.

Additional embodiments and features are set forth in part in the description that follows, and in part will become apparent to those skilled in the art upon examination of the specification or may be learned by the practice of the disclosure. A further understanding of the nature and advantages of the present disclosure may be realized by reference to the remaining portions of the specification and the drawings, which forms a part of this disclosure.

DESCRIPTION OF THE DRAWINGS

The description will be more fully understood with reference to the following figures, which are presented as exemplary embodiments of the invention and should not be construed as a complete recitation of the scope of the invention, wherein:

FIGS. 5A and 5B are tabular illustrations of potential evaluation parameters in accordance with embodiments of the invention.

FIGS. 17A and 17B illustrate a process flow for machine learning in accordance with embodiments of the invention.

DETAILED DESCRIPTION OF THE INVENTION

Figure 1:
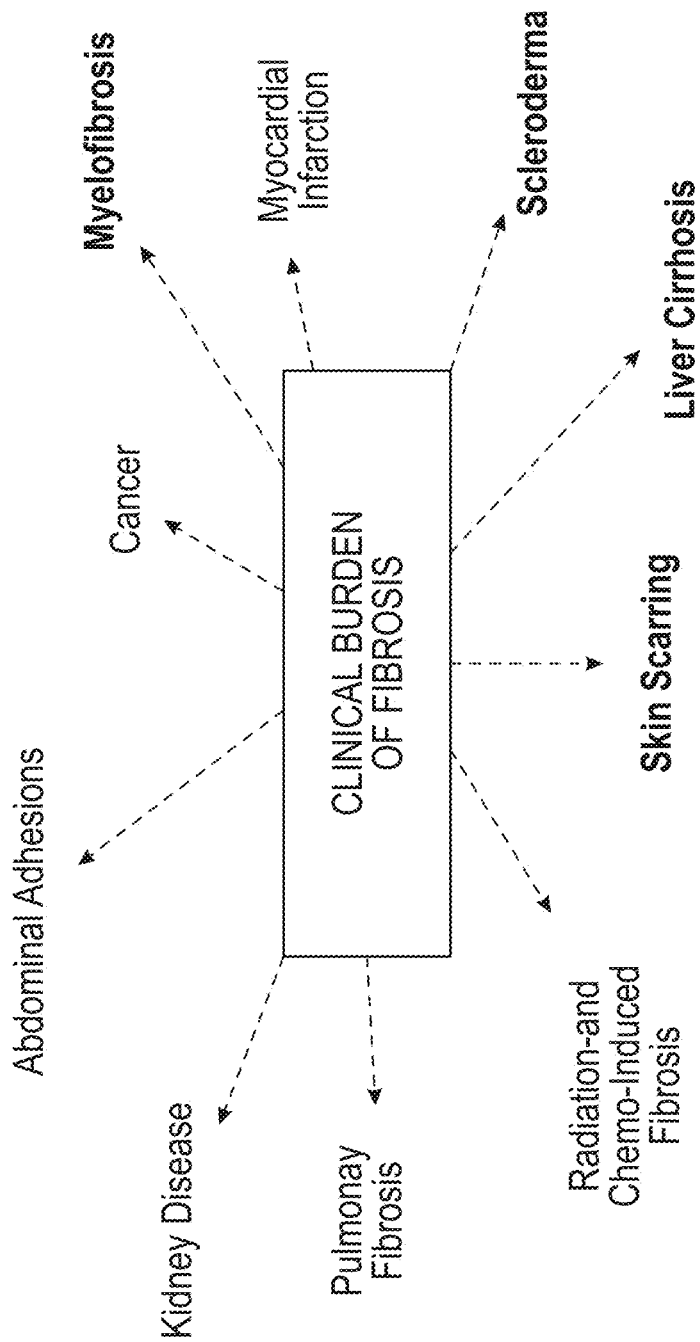
FIG. 1 illustrates a mind map of potential issues with fibrosis

Turning now to the drawings, embodiments of the invention include a method for automated connective tissue analysis using machine learning. In various embodiments, the method involves obtaining a plurality of images that may have been stained with one of a variety of staining methods. Staining methods may include, but are not limited to, Masson's Trichrome, Picrosirius Red, collagen immunostaining, and/or reticulin silver. In many embodiments the stained image can be processed for color deconvolution and cell subtraction to produce digital image maps of extracellular fibers and brachpoints. Once digital image maps are created, various embodiments can analyze the fibers against a number of parameters and then quantify and compare against prior data sets. Numerous embodiments can utilize the quantified data set to determine the extent of the fiber network. This information can be used to identify the type of fibrosis condition and the extent of it. Once the type and extent of the fibrosis is determined various embodiment can utilize the information to establish the appropriate treatment methodology for the respective patient.

Fibrosis poses a great financial and clinical burden on patients as well as medical professionals. Current methodology of analyzing fibrosis relies primarily on subjective clinical analysis of the tissues. Current diagnostic methods tend to be plagued by bias, inter-observer variability and poor sensitivity to subtle changes in disease status. Many pathologists can assign a score to tissue samples to determine the current state of the fibrotic condition. However, such scores tend to be very subjective, given the reasons above. Few objective, quantitative methods currently exist to reliably assess the presence or severity of fibrotic diseases. This is in contrast to pathologies such as cancer, where disease burden and chemotherapeutic efficacy can be measured quantitatively and non-invasively by standard-of-care modalities (MRI, PET-CT, etc.). Clinical management of fibroses instead relies on qualitative scoring schema (e.g., visual analogue scale, myelofibrosis score, Batts-Ludwig cirrhosis score) assessed by pathologists following visual examination of biopsied tissue. When tasked with subjective decision-making, physicians frequently rely on heuristics, or "rules of thumb" based on experience. While such mental shortcuts facilitate rapid judgment, they can lead to systematic errors and cognitive biases that are frequently associated with diagnostic and therapeutic errors. Furthermore, such approaches may fail to capture the spatial and morphological complexity common among fibroses.

In contrast, fully automated machine learning approaches based on connective tissue features, in accordance with many embodiments, can have immediate translational implications for clinical assessment of fibroses, including pathologic scarring (hypertrophic scars, keloids), systemic sclerosis, myelofibrosis, and cirrhosis. In accordance with various embodiments, the methods describe herein can improve sensitivity to clinically-undetectable skin fibrosis which can be particularly relevant for patients in the early stages of scleroderma, where the finding may drive treatment decisions and has predictive value for overall outcome. For example, while a pathologist scoring may score a patient's condition as a 1 on a scale of 1-4, various embodiments may be capable of improving the score that may be closer to a 1-4 rather than a 1 which can add value to the diagnosis and/or treatment of the condition. Furthermore, precise, objective quantification of the severity of myelofibrosis, liver cirrhosis, and other fibrotic conditions can augment staging, risk stratification, and therapeutic monitoring for these diseases Various embodiments can rapidly quantify thousands of extracellular matrix fibers across multiple imaging sites, thereby accurately reflecting the spatial heterogeneity in fibrosis. Accordingly, such methods have exhibited an AUC (area under the receiver operating characteristic curve) near or above 80% for all fibrotic pathologies studied to date, including areas of skin with "clinically-silent" skin fibrosis in systemic sclerosis. Therefore, many embodiments enable an objective approach that can significantly enhances the detection, diagnosis, and scoring of fibrotic diseases.

As described, it can be clinically important for both the medical professional as well as the patient to accurately and rapidly determine the severity of a fibrotic condition. Fibrosis can have various effects on the entire body and can lead to a number of life threatening conditions. For example, FIG. 1 illustrates a mind map of sorts that illustrates the potential burden of fibrosis. Fibrosis can be related to a number of different conditions such as cancer, myocardial infarction, scleroderma, and liver cirrhosis to name a few. Many of such conditions, if left untreated or even undiagnosed can lead to larger more long term health problems that can result on an unwanted burden on the patient. Moreover, improper or misdiagnosed conditions can result in costly medical treatments and/or potential legal complications.

Figure 2:
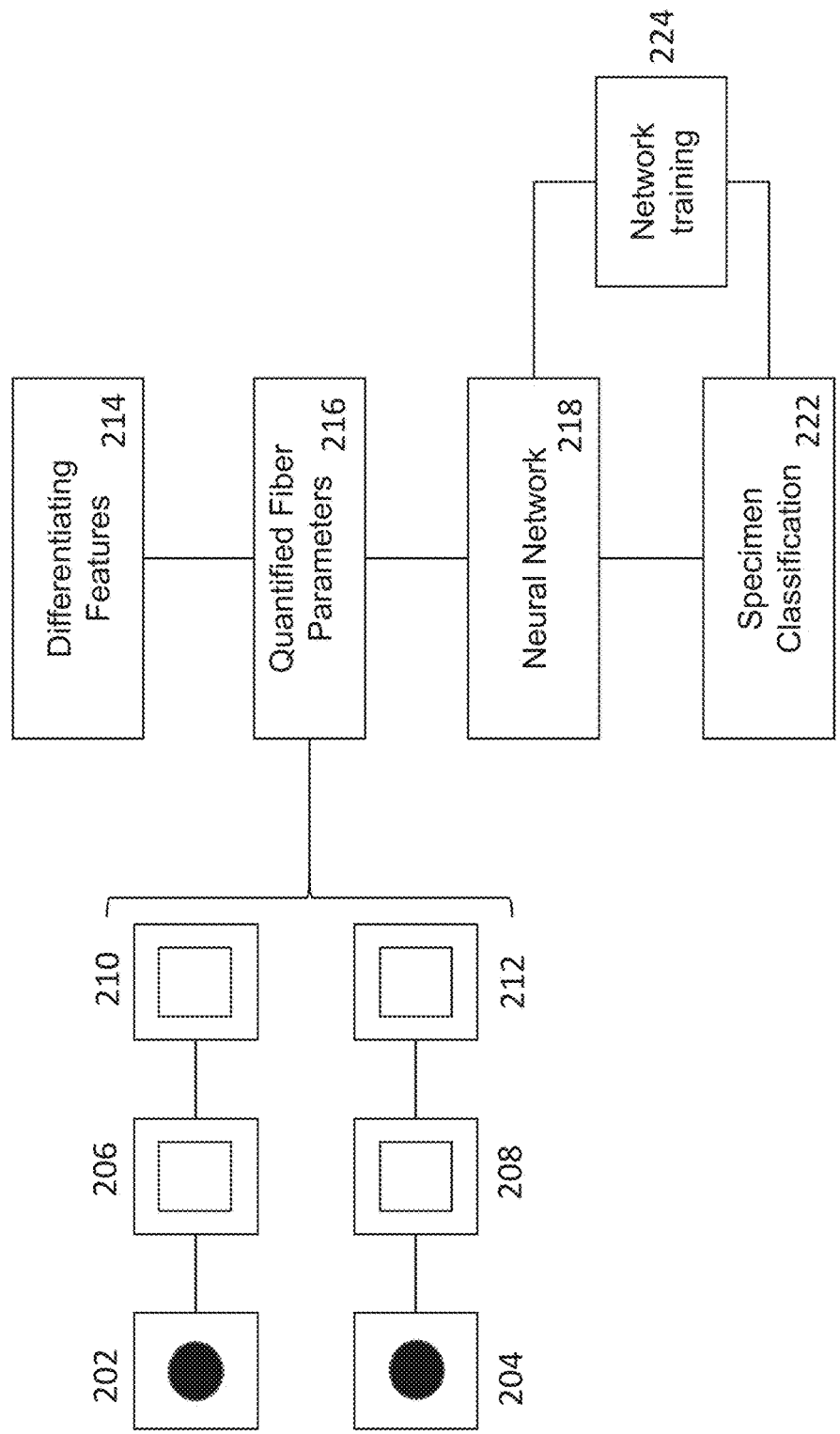
FIG. 2 illustrates a process of tissue analysis in accordance with embodiments of the invention.

In accordance with many embodiments, normal tissue can be compared to scarred tissue in order to best classify the level of fibrosis in the scared tissue. For example, FIG. 2 illustrates a comparison between normal 202 and scar 204 tissue that can be analyzed in a trained neural network for accurate tissue fibrosis classification. Tissue samples or images can be processed and analyzed in a number of different methods in order to establish a tissue classification. For example, some embodiments may identify a connective tissue histology (206 and 208) for each of the samples and then simplify the histology into a digital fiber map image (210 and 212) for the samples that can be used by various different machine learning techniques for tissue classification. In some embodiments, digital fiber map images can be used in a raw form in an unsupervised system to extract differentiating features 214 between the images. An unsupervised system looks for patterns in a data set that has not predetermined labels. In some embodiments, an unsupervised system can compare and contrast known images of fibrosis and normal skin with received images and evaluate the differences in order to classify the received image within a fibrotic disease classification and severity.

Alternatively, or conjunctively, some embodiments may utilize a supervised system to classify the images/samples into disease categories. A supervised system can evaluate a set of quantified fiber parameters 216 against the received processed images (210 & 212). Additionally, a supervised system can utilize a neural network 218 to fully evaluate the quantified parameters 216 against the images and classify each specimen 222 into a level of fibrosis. In accordance with many embodiments, the systems can be used to classify the images based on the disease and severity of it. Furthermore, the identification or classification of the images can be used to accurately diagnose the specific fibrotic condition which can be used in the treatment of the condition. In accordance with numerous embodiments, the classified image data 222 can be representative of a specific condition and can be utilized to further refine the analysis of future sample images. In other words, such classification data 222 can be used to further train the network 224.

Although the operations of some of the disclosed methods are described in particular, sequential order for convenient presentation, it should be understood that this manner of description encompasses rearrangement, unless particular ordering is required by specific language set forth below. For example, operations described sequentially may be, in some cases, rearranged or preformed concurrently. Moreover, for the sake of simplicity, the attached figures may not show the various ways in which the disclosed methods, systems, and apparatuses can be used in conjunction with other systems, methods, and apparatuses.

Embodiments of Image Processing

Figure 3:
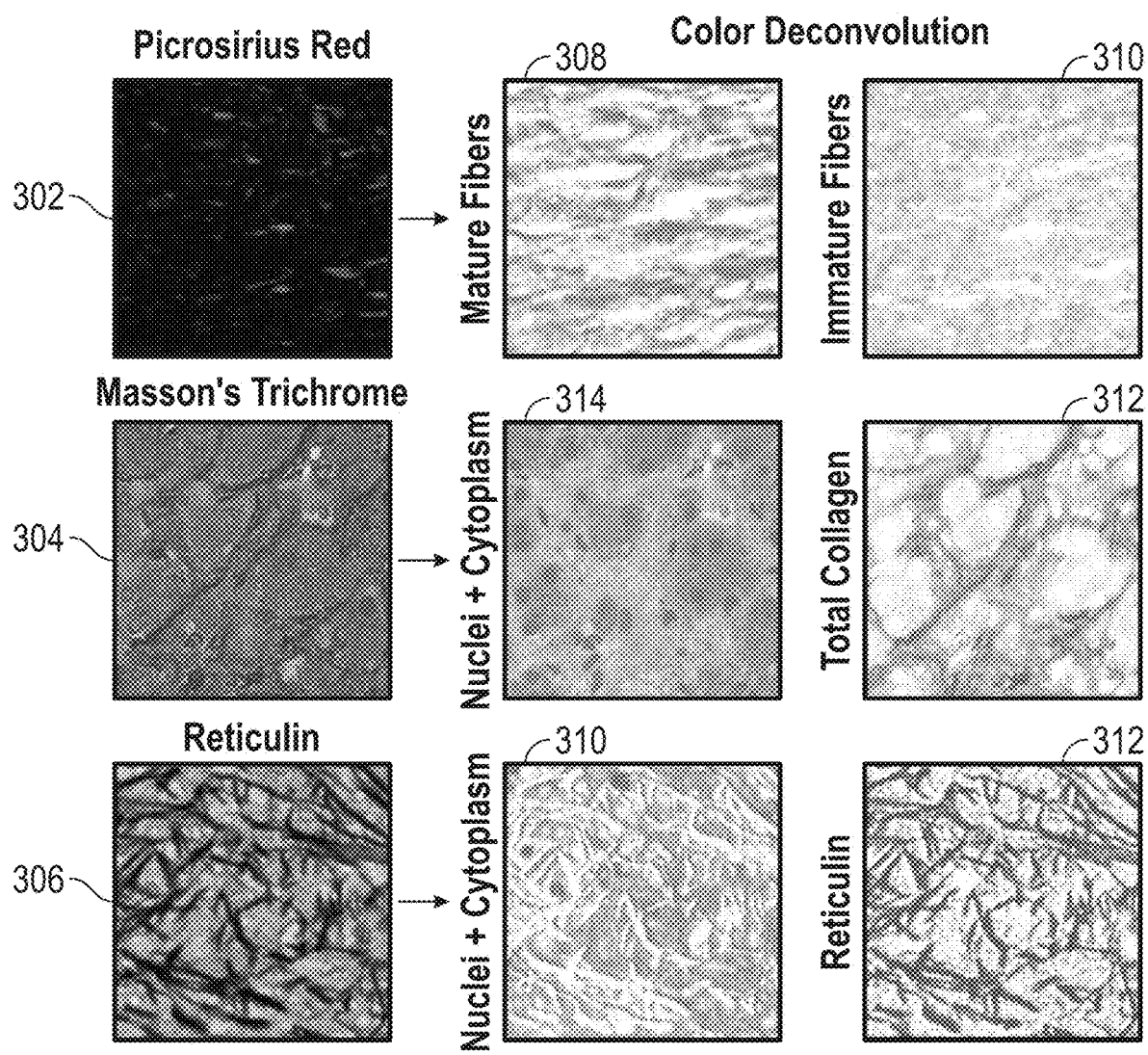
FIG. 3 illustrates an example of color deconvolution in accordance with embodiments of the invention.

As discussed previously many images or tissue samples can be stained in order to improve visibility in a variety of different uses, some of which can be helpful in diagnosing fibrotic conditions. However, color staining can often result in various noise or interference with the actual fiber networks within the sample and therefore may require some reduction of the image data or removal of the staining effects and/or cells in the image in order to extract the fiber networks for proper analysis and comparison. For example, FIG. 3 illustrates several stained tissue samples (302, 304, & 306) with different staining techniques. Some embodiments may use images with a Picrosirius red stain 302, or a Masson's Trichrome stain 304 and/or a reticulin stain 306. In accordance with many embodiments, the stained images can be processed by color deconvolution which is the reduction of the stained image into stain concentrations or a reduction of the color such that the fiber networks within the tissue sample can be isolated for better analysis. For example a Picrosirius red stain can be reduced to red mature fibers 308 and green immature fibers 310. Likewise, tissue samples stained with other staining techniques can be deconvoluted into the tissue portions such as total collagen 312 and nuclei and cytoplasm 314 in Masson's Trichrome. It can be appreciated that a variety of staining techniques can be used and that such stained samples can be deconvoluted in order to better evaluate the fiber networks within the respective tissue samples.

Figure 4:
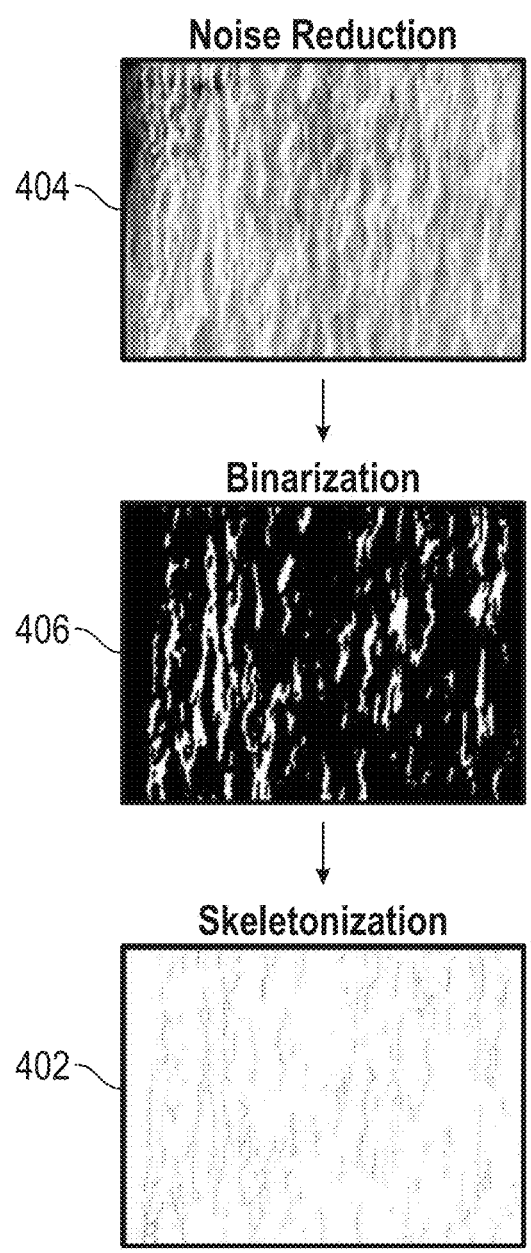
FIG. 4 illustrates a down trace function of skeletonizing a sample in accordance with embodiments of the invention.

Although the process of color deconvolution is well established, many embodiments may incorporate further processing of images in order to identify the fiber network within the sample. For example, in various embodiments deconvoluted sample images as seen in FIG. 3, can be further processed or simplified in a number of ways to isolate and clarify the fiber network within the sample image. For example, FIG. 4 illustrates a process by which a deconvoluted sample image, similar to those in FIG. 3, can be further processed into a simplified or skeletonized image 402 of fibers. A skeletonized image 402 refers to the fiber(s) within the sample image are reduced to linear structures that can be analyzed in order to determine the level of fibrosis within the sample. The skeletonized image 402 essentially creates a digital fiber map against which a number of parameters can be quantified. In numerous embodiments, the digital fiber map 402 may be produced by a number of different refinement methods. For example, a noise reduction method 404 can be used to smooth the image and better define the fiber images. In some embodiments, the noise reduction can be done with an adaptive edge preserving noise reduction method. Various embodiments may process the sample image by binarization and/or shape-based selection of fiber shaped objects 406. Binarization essentially represents the image as 1's and 0's where the 1's define the pixels containing fibers. Subsequently, the sample image can be further down traced to reflect the digital fiber map 402 that can be used and/or compared against a set of parameters to establish the category and/or severity of the fibrotic state. Essentially the image processing can remove cells and can leave behind a fiber network of individual fibers that can be further analyzed in order to assess the level of fibrosis present. It can be readily appreciated that within each level of image processing that the existing fiber networks can demonstrate a number of different quantifiable parameters that can be used in the subsequent analysis of the images.

The various embodiments described herein illustrate image processing that can be performed on any number and type of images. Embodiments illustrate the applicability of various image processing techniques that can be used in conjunction with other systems and methods in order to analyze the images for parameter quantification and subsequent fibrosis diagnosis and treatment.

Embodiments of Image Analysis

The analysis of the sample images can be done in a number of ways. As previously discussed, some embodiments may utilize unsupervised and/or supervised systems to evaluate and/or compare the digital maps in order to classify the received sample image and subsequently diagnose the severity and status of the fibrosis. An unsupervised system can compare a received sample image against previously known images stored in a database such that the received image can be differentiated and used to determine the fibrosis condition. This can be done without necessarily reducing the fiber image into the skeletonized form.

In some embodiments, a supervised system can compare and/or evaluate the sample image against a list of parameters. In other words, a supervised system can utilize a fully skeletonized image and evaluate the image based on the supplied set of weighted parameters. FIGS. 5A and 5B illustrate various parameters and their respective descriptions that can be quantified in the image analysis process for determining the level of fibrosis during the machine learning techniques. The parameters may be weighted based on their relation to specific fibrotic conditions and/or other quantified parameters of the tissue image sample of fibers. Parameters can include, but are not limited to physical characteristics such as the number of fibers, the length, width, and/or alignment of the fibers in the sample image(s). Such parameter types may be well-known and understood, however, various embodiments can include less well-known attributes such as Euler number, which quantifies the holes within each fiber. It can be appreciated that any number of parameters can be used and that the list of parameters can be expanded upon though embodiment which apply a machine learning process. For example, in numerous embodiments the level of fibrosis or fibrotic condition can be quantified and compared to the fiber level across a large panel of properties. This can be further enhanced with the application of machine learning processes.

The list of parameters illustrated in FIGS. 5A and 5B are representative of a few of the many potential parameters that can be quantified with respect to the image sample. However, it can be appreciated that new parameters can be incorporated and weighted as new images are analyzed. For example, FIG. 5B illustrates a list of additional parameters that may be quantified and weighted for the particular tissue image sample that extends beyond those illustrated in FIG. 5A. The listing of parameters is not necessarily specific to each tissue sample, but can vary from sample to sample. Additionally, quantified parameters can vary based on the staining technique as well as the level of image processing. For example, some embodiments may be able to quantify a number of different parameters based on a simple stained image, similar to FIG. 3, without any subsequent processing. Other embodiments may quantify a number of different parameters for a deconvoluted images which may be different from the quantified parameters for a skeletonized or binary image. Likewise, the number and type of quantified parameters can vary if the stained image is that of Picrosirius red, or Masson's Trichrome, Reticulin, Such embodiments can improve the overall analysis capabilities of the systems and methods described herein by teasing out minute differences in the tissue sample images. As new parameters are discovered and/or weighted they can be quantified in subsequent analysis of tissue image samples. Thus, they can be useful in improving the capabilities and sensitivity of the analysis. Accordingly, improved sensitivity can allow for improved diagnosis of the respective patient and can help to develop an effective treatment plan.

Figure 6A:
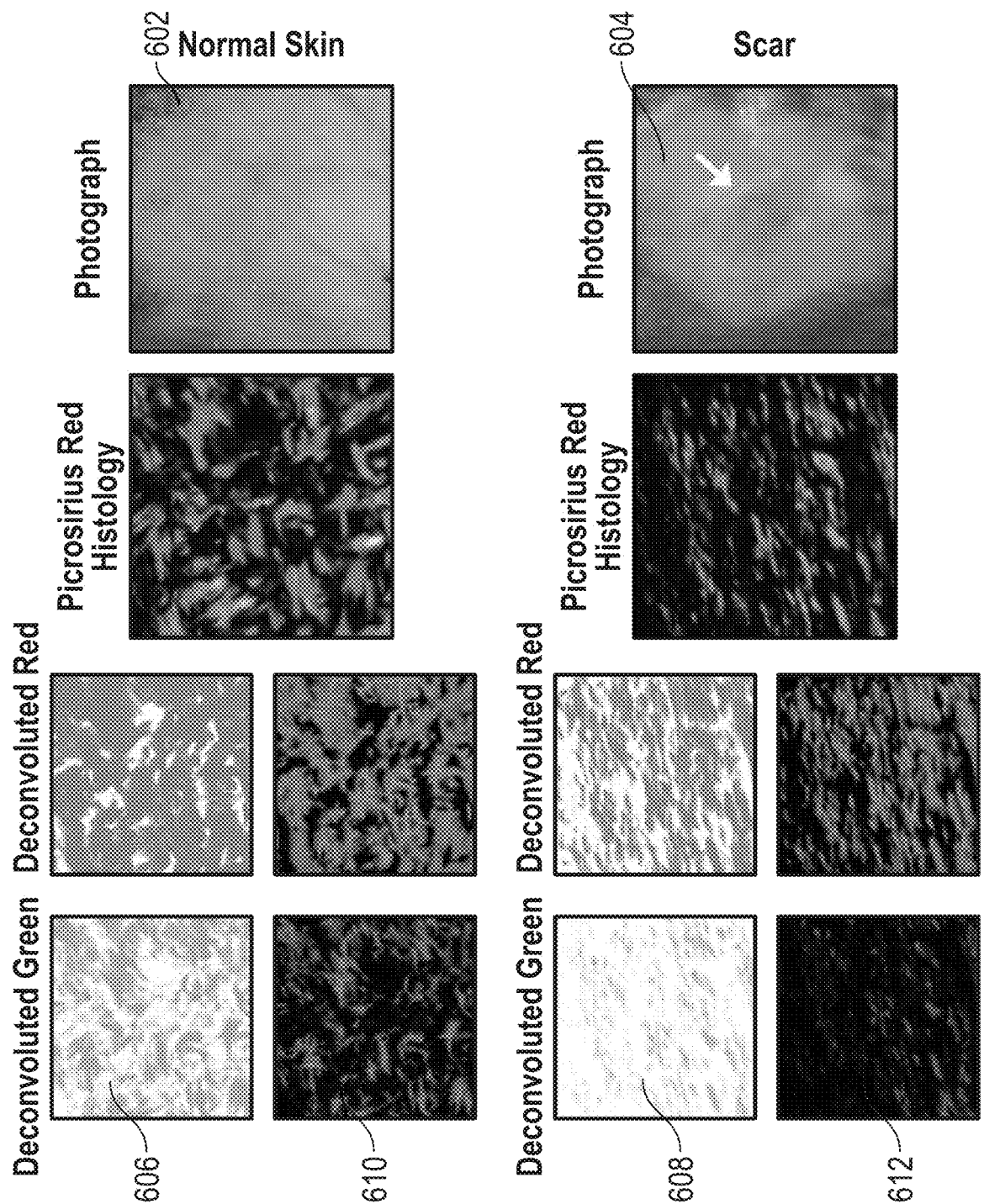
FIG. 6A illustrates images of scar and normal tissue for analysis.
Figure 6B:
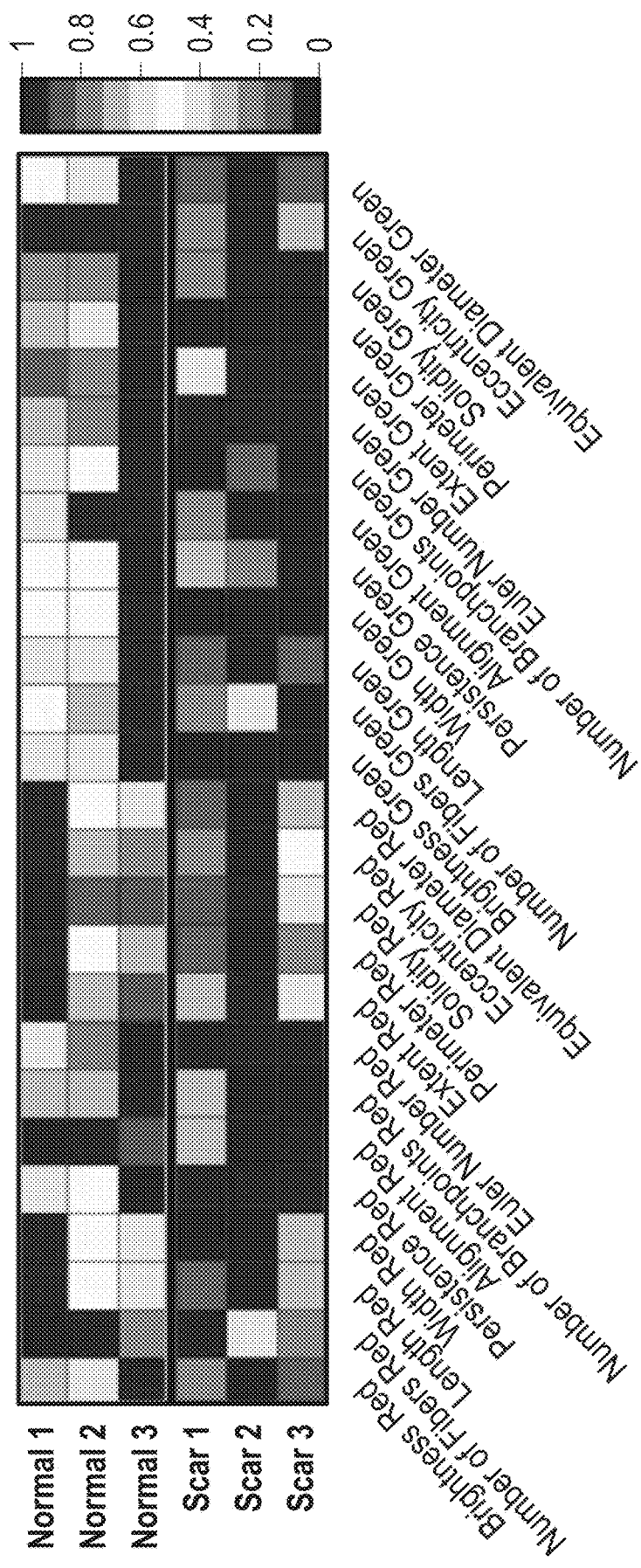
FIG. 6B illustrates a heat map comparison between normal and scar tissue for a variety of parameters in accordance with embodiments of the invention.
Figure 6C:
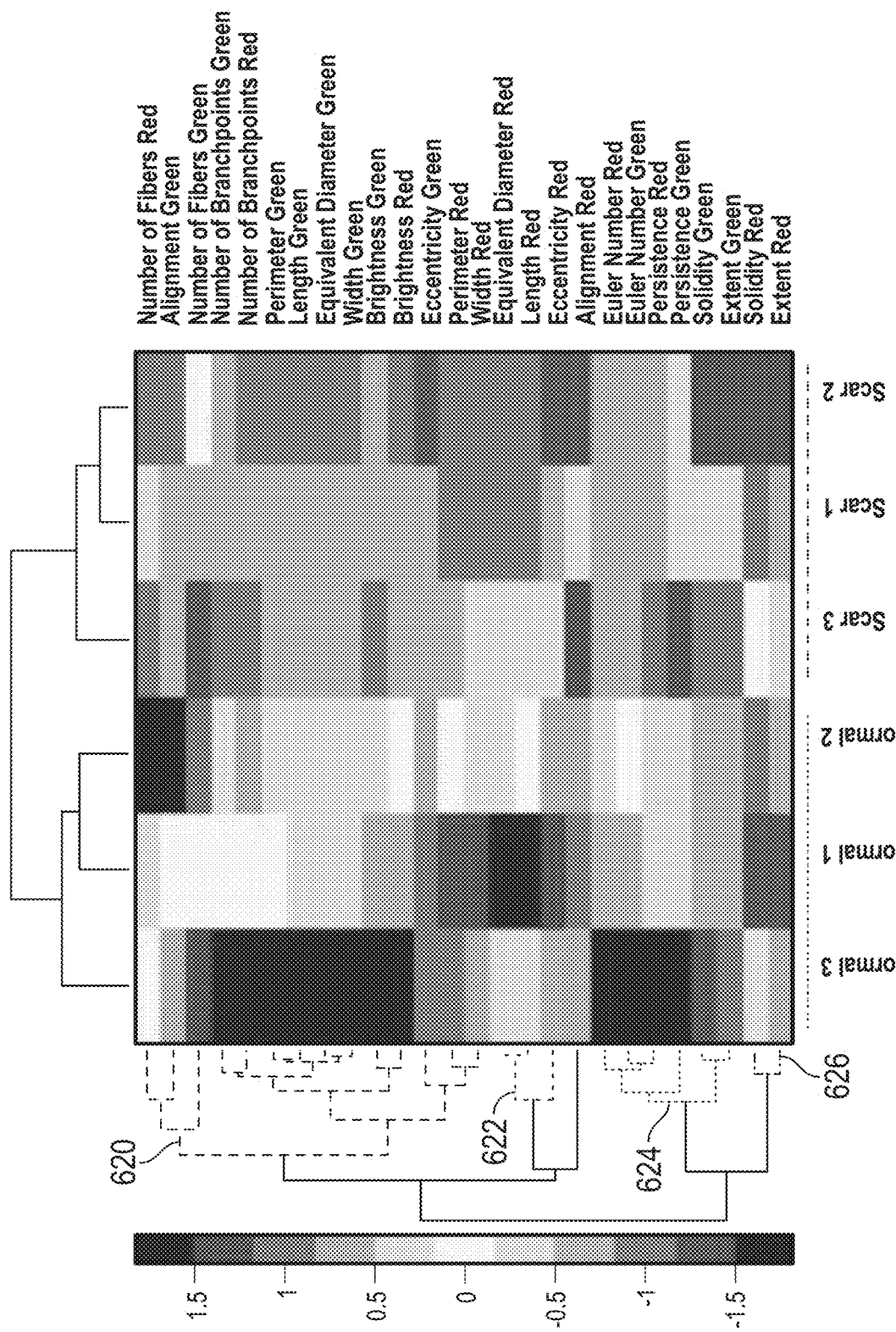
FIG. 6C illustrates a clustering of parameters in accordance with embodiments of the invention.

FIGS. 6A through 6C illustrate an example of a stepwise analysis of two different tissue samples for comparison in accordance with various embodiments. For example, FIG. 6A illustrates two tissue samples, normal 602 and scarred 604 which can be processed by color deconvolution 606 and 608 as well as noise reduction to produce digital network maps 610 and 612. FIG. 6B illustrates a heat map evaluation of the various parameters for each of the scarred and normal tissue sample images for both the deconvoluted red 606 and green 608 images for both. In certain embodiments, each parameter of the fiber image can be rated or scaled on from zero to one. It can be seen that normal and scarred tissues can produce distinct overall connective tissue patterns that illustrate different levels of fibrotic healing. Additionally, different images from the same tissue can be compared as can be seen in FIG. 6B. Further, it can be illustrated the upper section of the heat map is distinct from the lower section thereby illustrating the distinct pattern differences between scarred tissue and normal tissue. The information provided in a generated heat map similar to that in FIG. 6B can be stored for use for further analysis in some type of memory device.

In various embodiments, machine learning systems, such as processors, can utilize the parameter characterization illustrated in heat maps and subsequently stored to generate clusters of similar datasets or similar parameters. For example, FIG. 6C illustrates a hierarchical clustering of data from several normal and scarred processed images. It can be seen that normal and scarred fibers will cluster into distinct groups (620-626). The hierarchical clusters are essentially parameter clusters that can be used to further determine the fibrosis condition and/or severity present in the tissue sample. It can be appreciated from the parameter clustering and differentiation in the image samples can vary from patient to patient as well as from sample to sample within a single patient. This can be helpful in the ultimate diagnosis of the level of fibrosis in within the patient as well as providing useful information for future diagnosis.

Figure 7A:
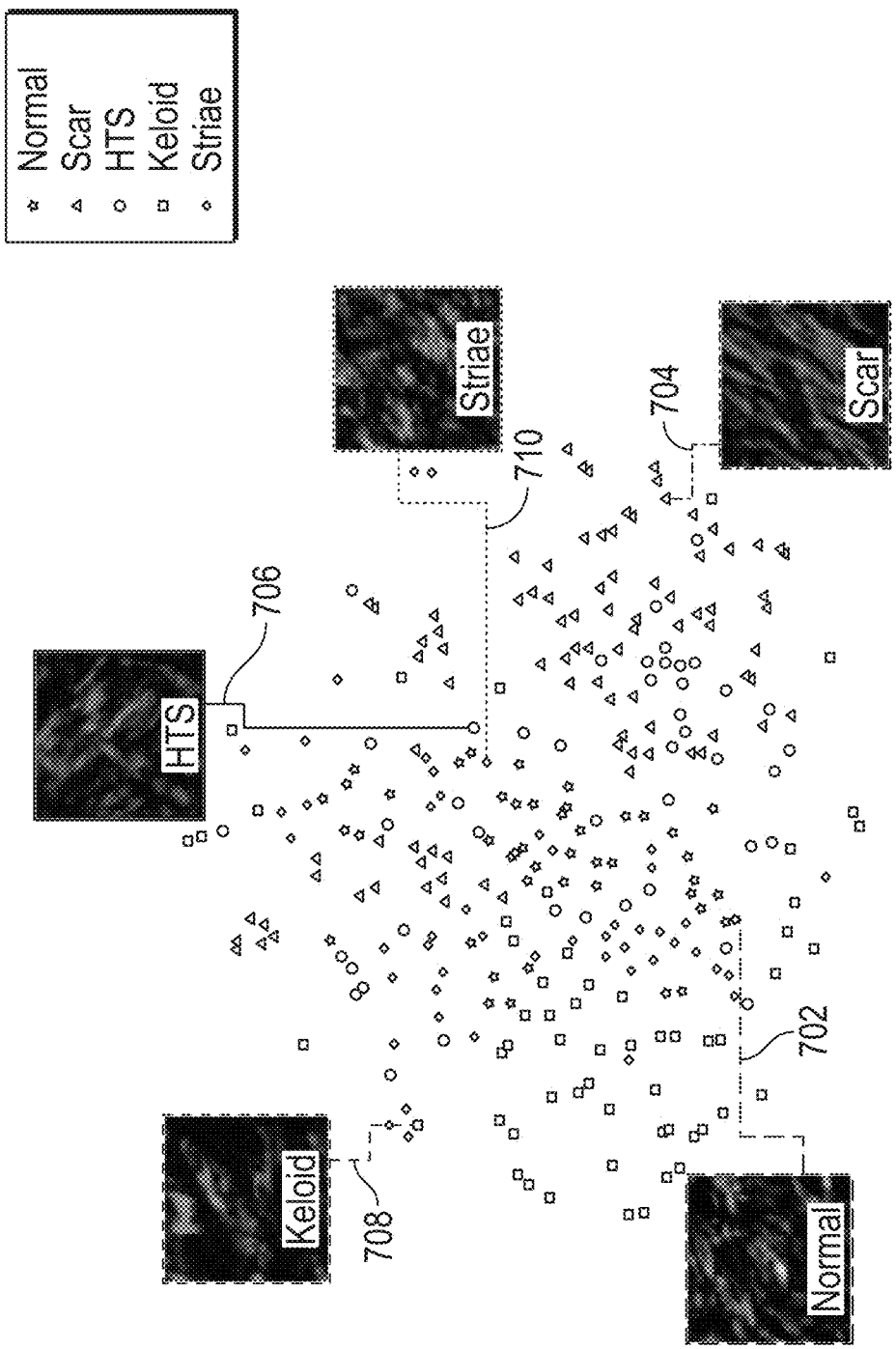
FIG. 7A illustrates a clustering of tissue fiber characteristics in accordance with embodiments of the invention.
Figure 7B:
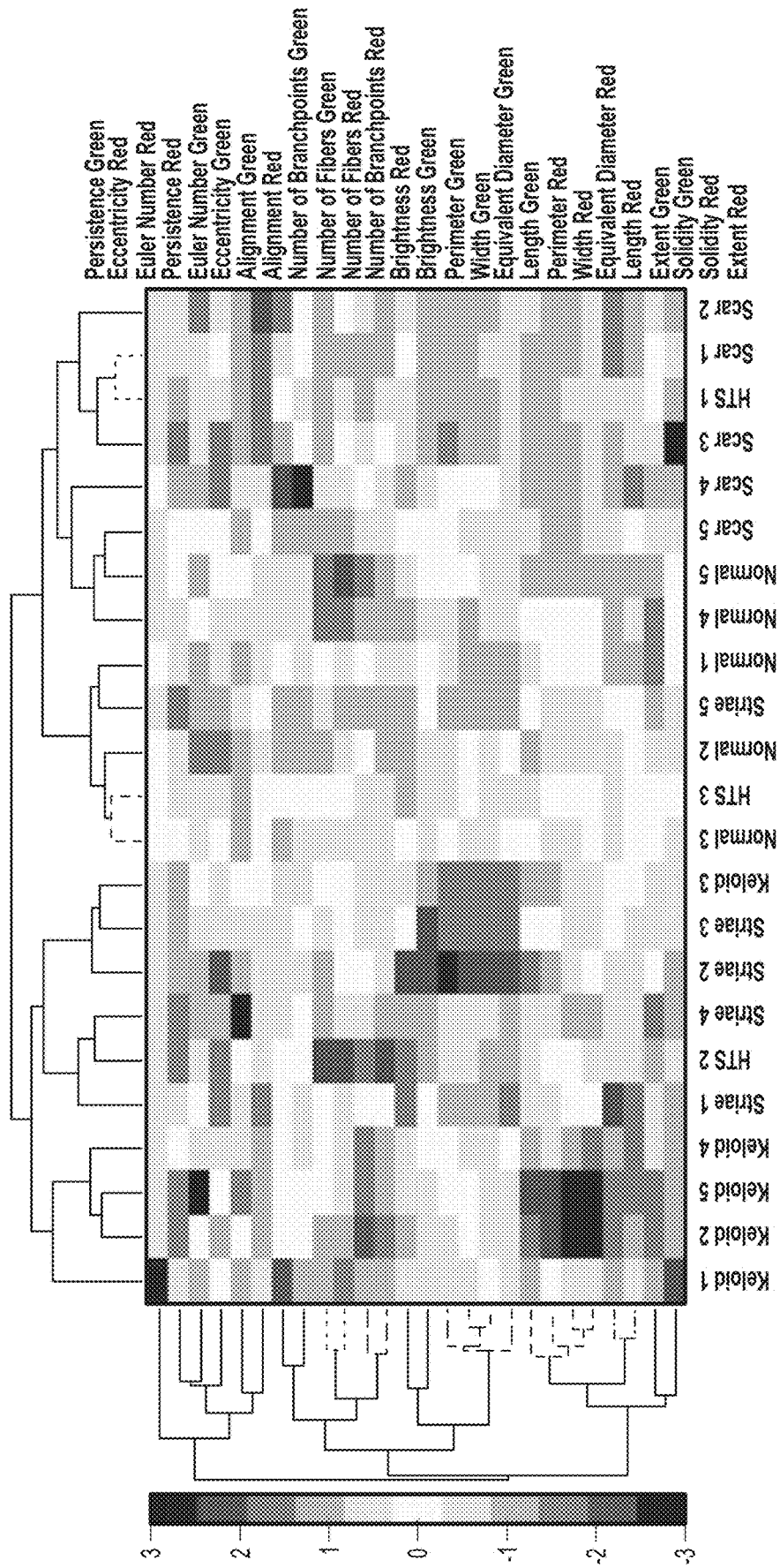
FIG. 7B illustrates a hierarchical clustering of quantified parameters for various tissue samples in accordance with embodiments of the invention.

Fiber clusters can also be illustrated in non-deterministic visualization such as illustrated in FIG. 7A. It can be appreciated that such clustering illustrates specimens can cluster according to their known type such as normal tissue 702, normal scar 704, hypertrophic scar (HTS) 706, Keloid 708, and/or Striae 710. Comparatively, heat map data and subsequent hierarchical clustering illustrates the ability to cluster data in accordance with the specific condition as well as the tissue sample. For example, FIG. 7B illustrates a hierarchical clustering of the data illustrated in the heat map of FIG. 7A This grouping based on the established set of parameters for the image processing can be beneficial as it can be illustrated that like fibers tend to group together illustrating a fibrotic. It can be further appreciated that many embodiments can be capable of determining the level of fibrosis in patients that have no clinical symptoms thereof based on the formation of the digital fiber map images and subsequent analysis. Thus, many embodiments can utilize clustering of image data to establish a diagnosis which can be beneficial in the early detection and subsequent treatment of fibrotic conditions.

Figure 8:
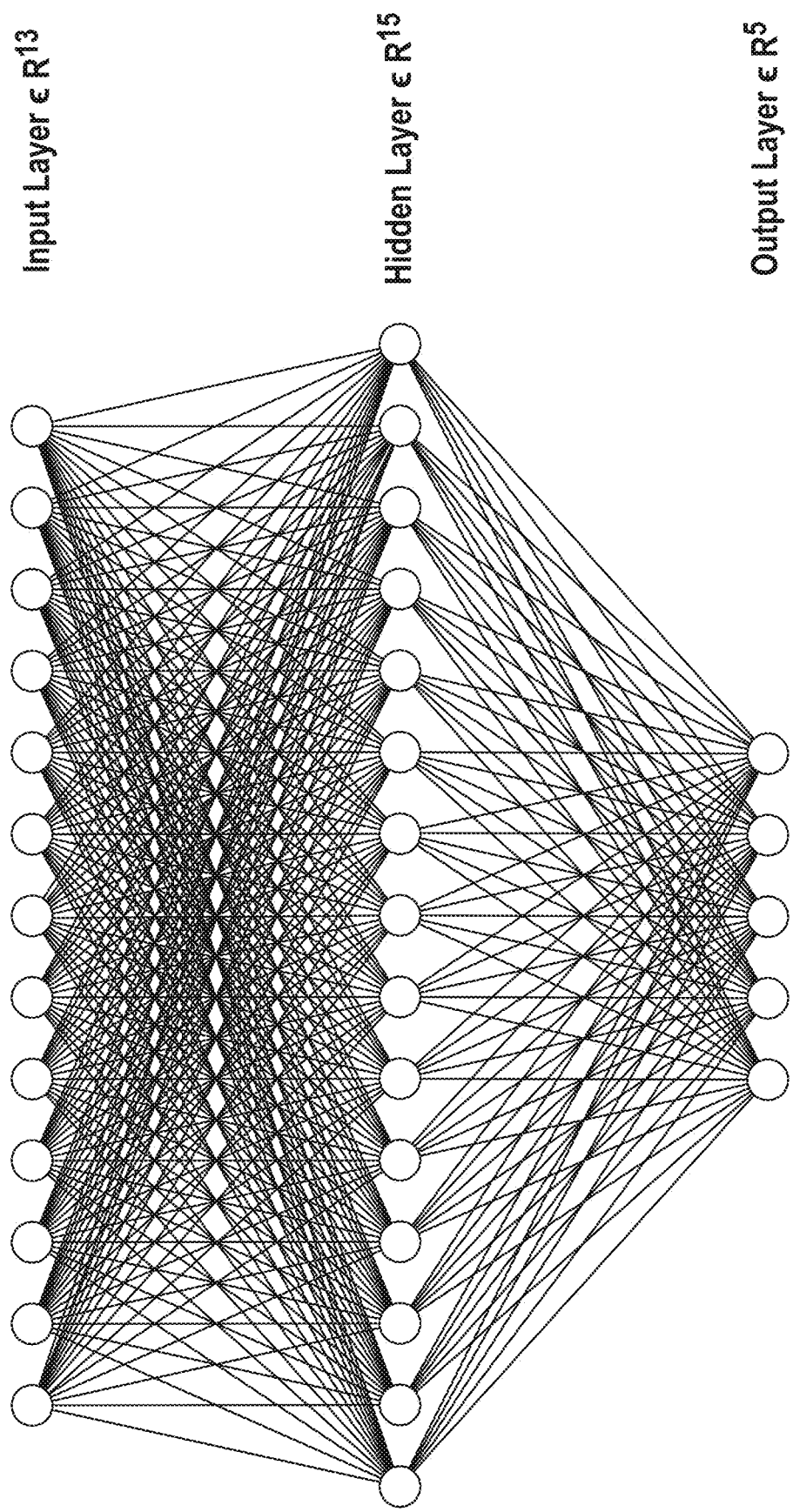
FIG. 8 illustrates a neural network diagram to analyze and compare tissue samples in accordance with embodiments of the invention.

As previously discussed, many embodiments may use neural networks that can be trained to effectively and efficiently evaluate the processed images for the various parameters that may be useful in indicating a particular fibrotic condition. For example, FIG. 8 illustrates a neural network configuration that may be used in some embodiments. In many embodiments, the neural network can have multiple layers of data for analysis. An input layer may consist of any number of neurons that may correspond to the various input parameters needed to effectively analyze the processed images. Additionally, many embodiments may have one or more hidden layers for further processing the image data. Finally, various embodiments may have one or more output neurons in an output layer which corresponds to the desired output (or classification) of the images. For example, some embodiments may be looking to identify one or more particular fibrotic conditions such as Keloids or HTS or any number of fibrotic conditions including sclerosis.

Figure 9:
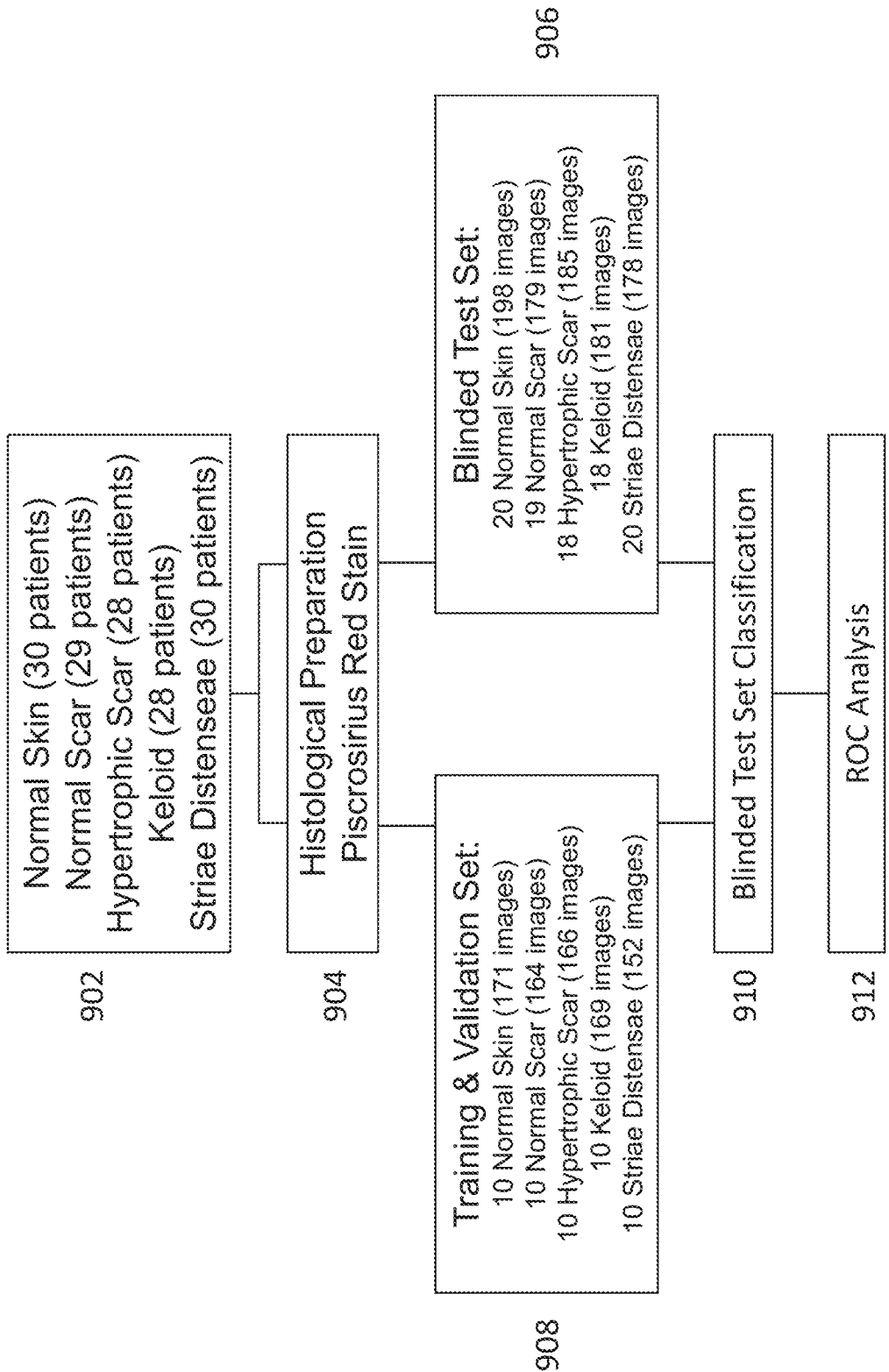
FIG. 9 illustrates a flow chart of analyzing tissue data sets with neural networks in accordance with embodiments of the invention.

Referring to FIG. 9, a consort diagram represents a process flow used in an example operation in accordance with some embodiments to analyze a number of image samples of known fibrotic conditions to illustrate the effectiveness of a trained neural network in classifying images. The image samples 902 are representative of a number of different fibrotic conditions. The images all have been prepared using a Picrosirius red stain 904. The images were processed and analyzed in a blind test 906 and a data set using a trained neural network 908 in order to evaluate the effectiveness of the trained neural network. Subsequently the blind test data was classified by neural network 910 and analyzed under a Receiver Operator Characteristic (ROC) curve 912.

Figure 10:
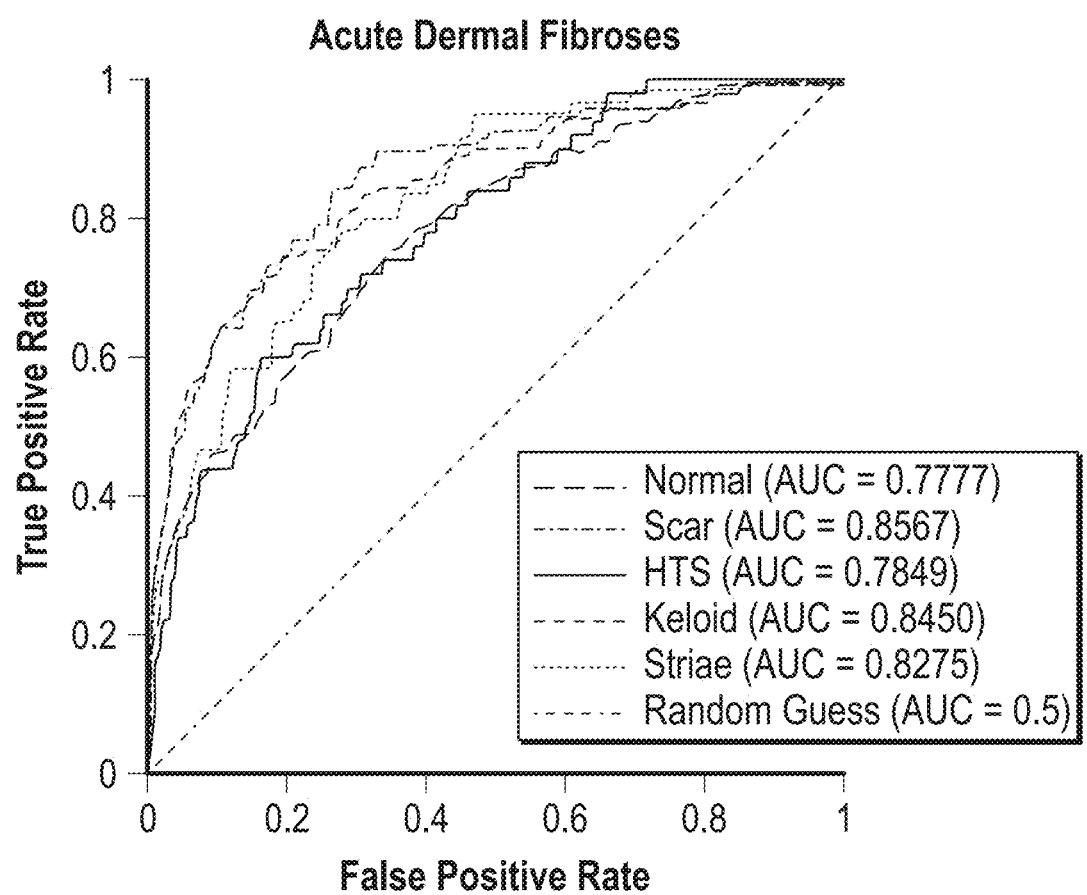
FIG. 10 illustrates Receiver Operating Characteristic (ROC) curves for various tissues in accordance with embodiments of the invention.

FIG. 10 illustrates the ROC curve of the example illustrated in FIG. 9. The graph compares false positive rate along the x-axis to the true positive rate for all five classifications of images. As can be seen the data sets hug the upper corner of the plot which can be appreciated as illustrating a sensitive analysis process. It can be appreciated that the area under the ROC curve illustrates the improved capability of many embodiments of analyzing image data to accurately recognize specific characteristics of different levels of fibrotic conditions. For example, in many embodiments the trained neural networks are sensitive enough to distinguish between normal skin, normal scars hypertrophic scars, keloids, and/or straie based on their connective tissue network properties. Although only five fibrotic conditions are illustrated, it can be appreciated that many embodiments may utilize neural networks capable of being sensitive to any number of fibrotic conditions.

Figure 11A:
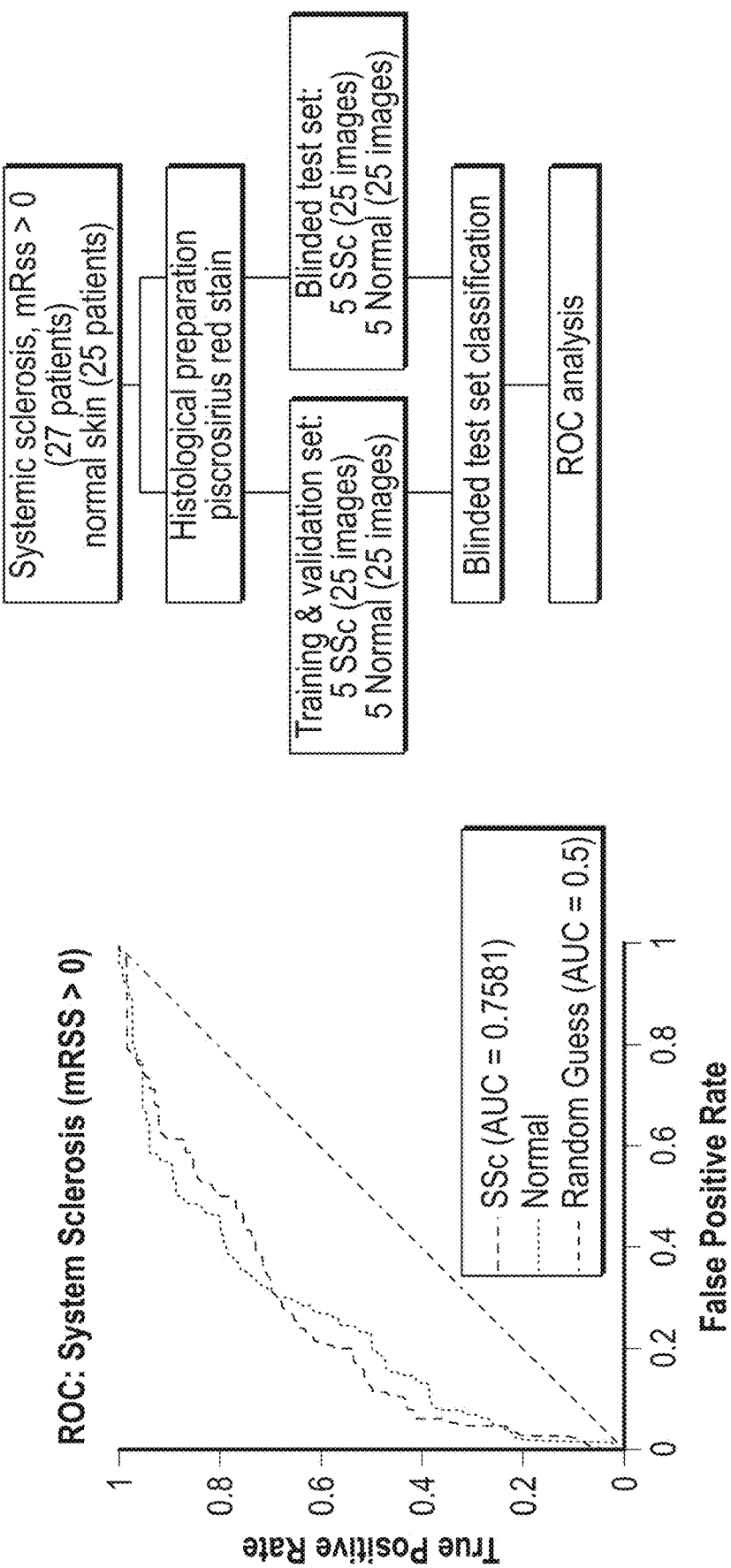
FIGS. 11A and 11B illustrate ROC curves and flow chart analysis in accordance with embodiments of the invention.
Figure 11B:
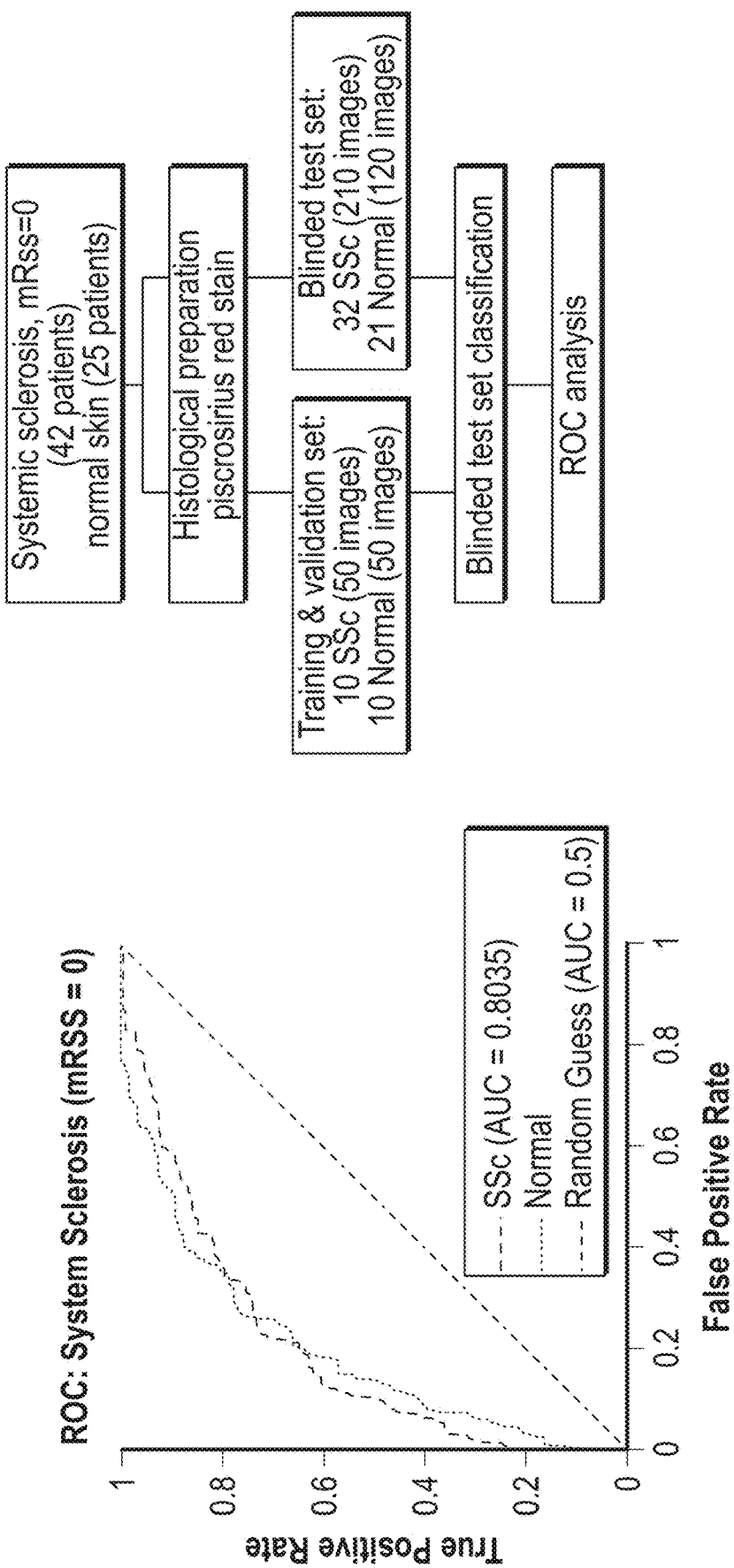

For example, FIGS. 11A and 11B illustrate comparative ROC plots and associated cohort diagrams for image data related to systemic sclerosis. FIG. 11A illustrates an ROC curve of a neural network's performance in classifying images of normal skin and samples from patients with clinical evidence of systemic sclerosis. FIG. 11B illustrates an ROC curve of a neural network's performance in classifying sample images from a patient with clinical evidence of systemic sclerosis. The sample images were from both normal tissue as well as fibrotic tissue. It can be appreciated that the respective curves illustrate the network's sensitivity and capability of detecting the various levels of a fibrotic condition. The graphs illustrate the ability of many embodiments to detect different levels and progression of a particular disease.

Figure 12A:
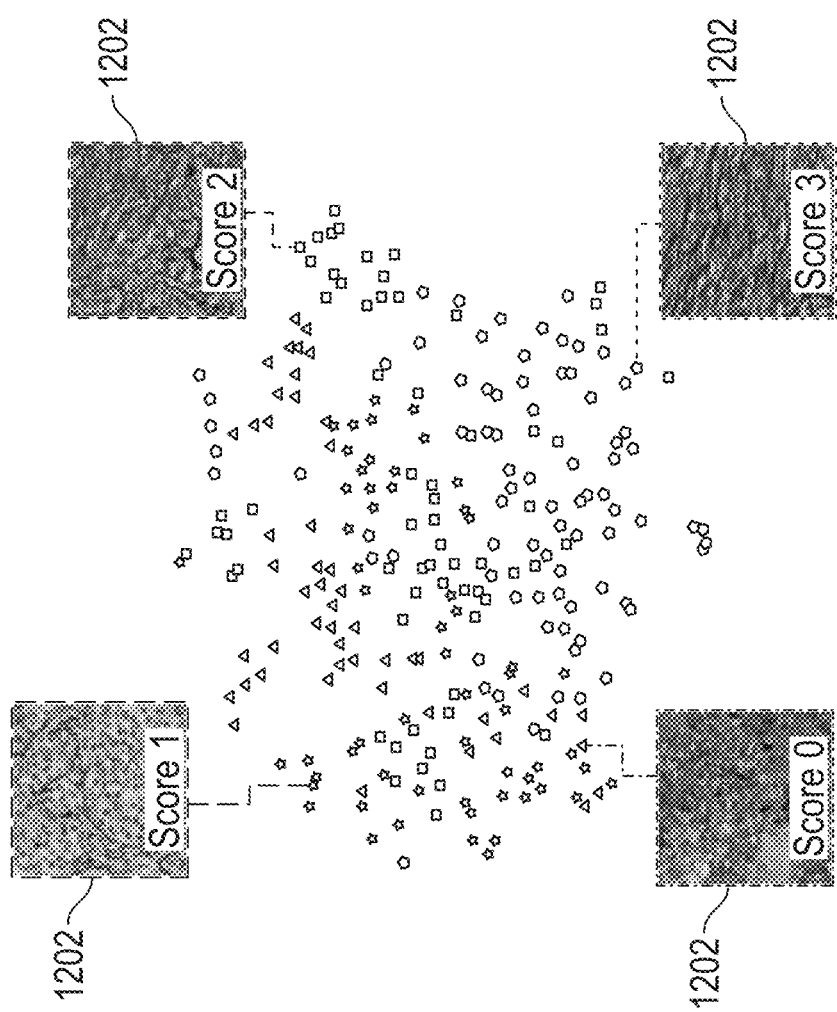
FIG. 12A illustrates a clustering of tissue fiber characteristics in accordance with embodiments of the invention.
Figure 12B:
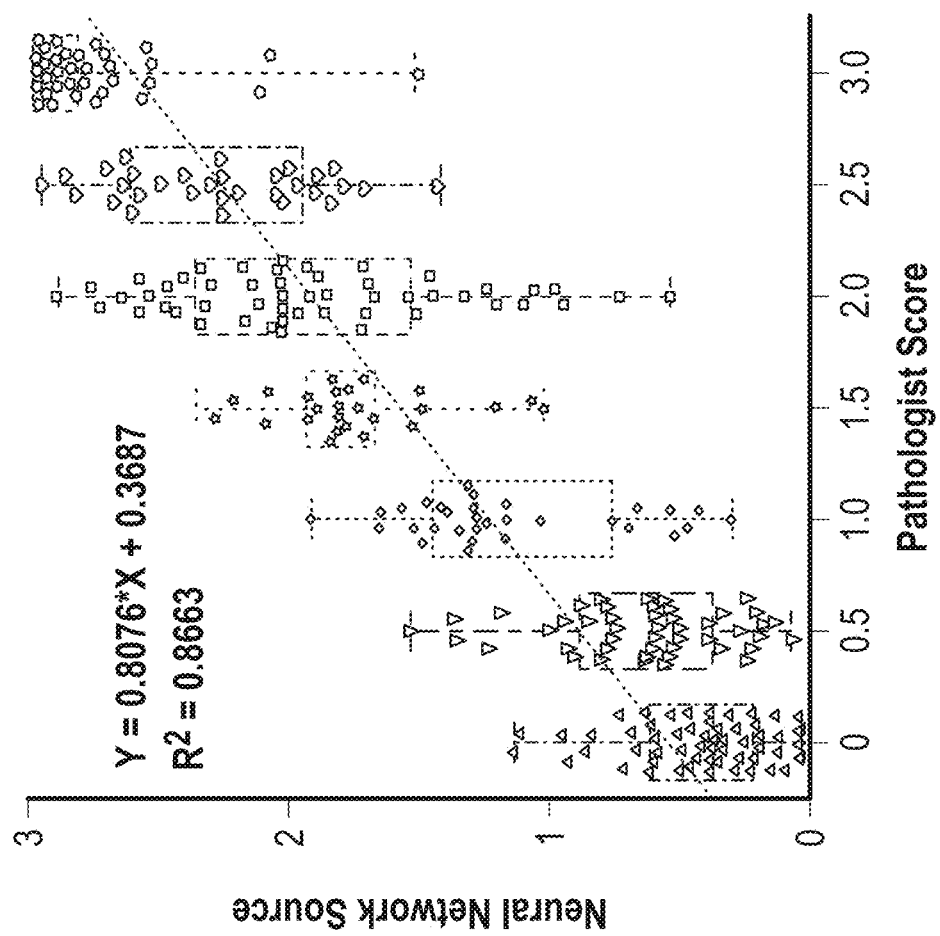
FIG. 12B illustrates a comparison between neural network data analysis and human pathologist evaluation in accordance with embodiments of the invention.
Figure 13A:
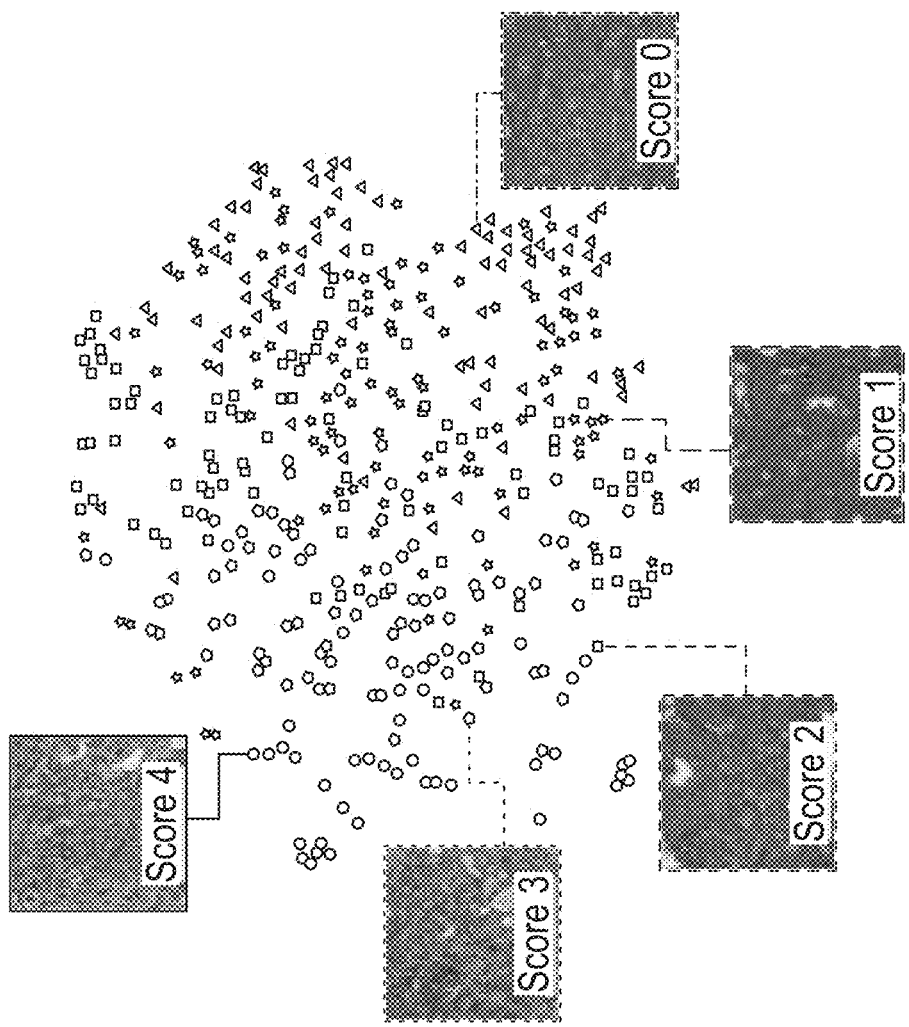
FIG. 13A illustrates a clustering of tissue fiber characteristics in accordance with embodiments of the invention.
Figure 13B:
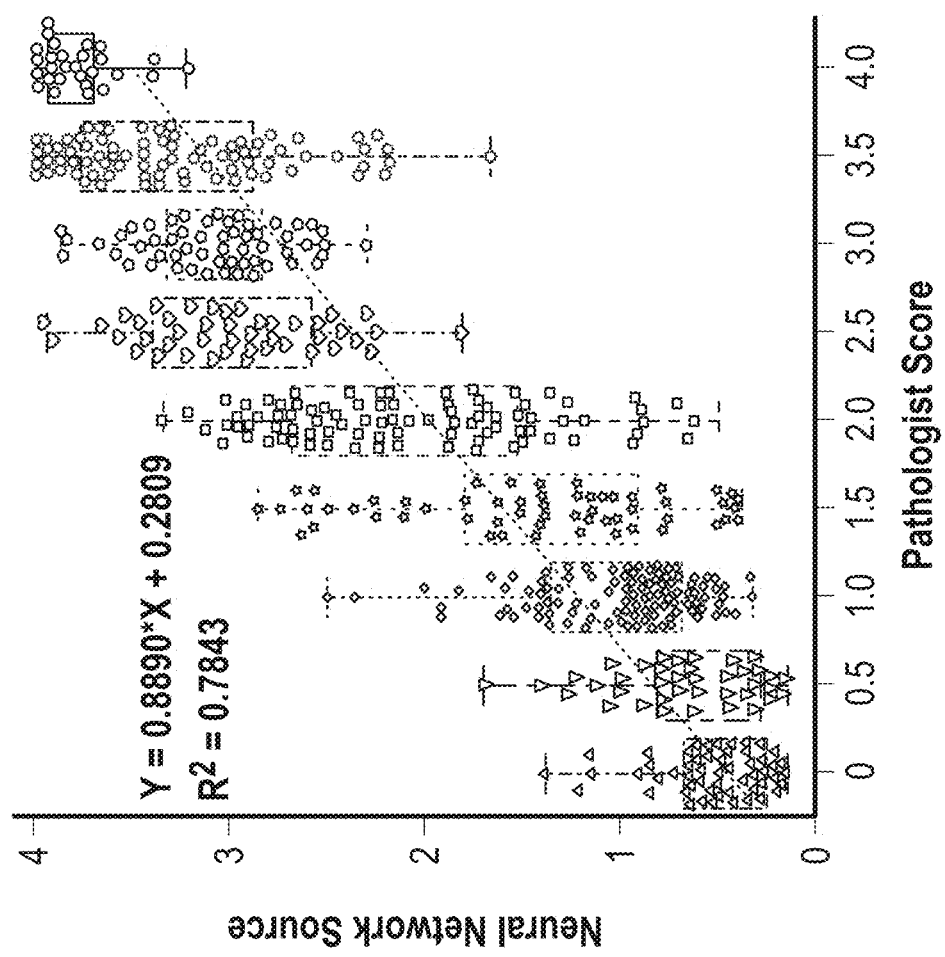
FIG. 13B illustrates a comparison between neural network data analysis and human pathologist evaluation in accordance with embodiments of the invention.

FIGS. 12A through 13B illustrate output data sets from various embodiments of a neural network analysis when compared to the tissue analysis of a pathologist for Myelofibrosis and Cirrhosis respectively. FIG. 12A illustrates a data clustering of image data based on myelofibrosis disease intensity level. The analysis produced four different clusters with intensity scores ranging from 0 to 3 (1202 to 1208). FIG. 12B illustrates the comparison between the neural network analysis and that from a pathologist for similar data sets. It can be appreciated that the neural network analysis can be more sensitive to changes in disease intensity level in among the mid-range scores than the pathologist. Thus, it can be appreciated that many embodiments offer improved capabilities over more traditional pathological analysis. Likewise, FIGS. 13A and 13B illustrate similar capabilities over intensity scores ranging from 0 to 4 representing 5 distinct clusters (1302-1310). Accordingly, the neural network demonstrated improved capabilities among the mid-range scores and similar sensitivities on the extreme scores as that of a pathologist.

Figure 14A:
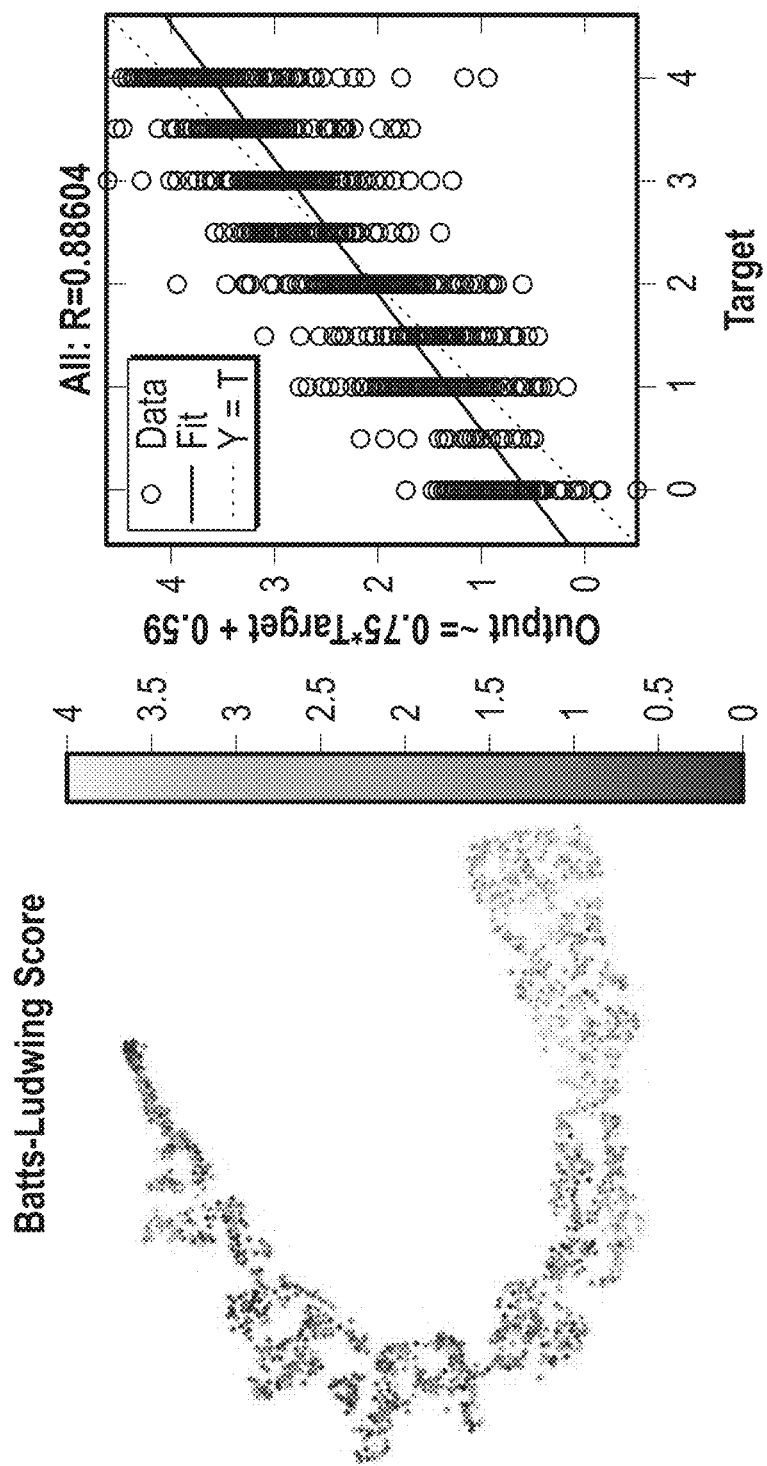
FIGS. 14A and 14B are graphical illustrations of a fibrotic condition quantified across 294 parameters in accordance with embodiments of the invention.
Figure 14B:
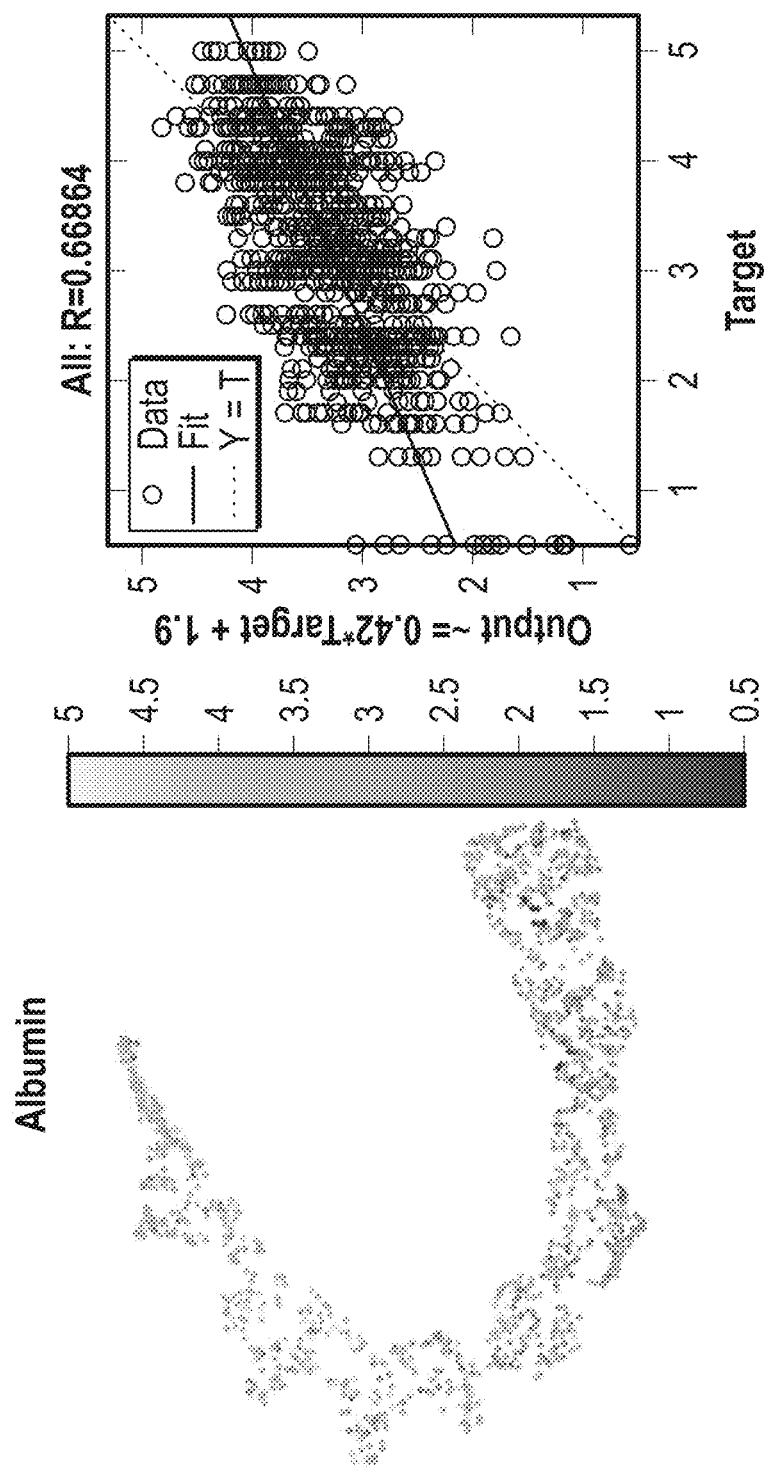

As previously described with respect to FIGS. 5A and 5B, numerous embodiments may utilize an expanding number of parameters that can be quantified against the tissue image samples. For example, FIGS. 14A and 14B illustrate various t-SNE (T distributed Stochastic Neighbor Embedding) plot of liver cirrhosis compared across 294 parameters. It can be illustrated that the separation between severities of the disease is improved with a greater parameter set as compared to the data illustrated in FIGS. 6 through 13B. In accordance with various embodiments the machine learning algorithms can continue to learn and expand upon the number of parameters, thus helping to improve the sensitivity of the system across the data set to illustrate the different levels of severity of the respective disease. It can be appreciated further when comparing such increased parameters that the improved sensitivity can provide an effective diagnostic tool. Furthermore, improved diagnosis can help medical providers to more effectively establish treatment plans that are targeted towards the specific level of the disease. For example, depending on the severity level of the disease different treatment plans can be established, such as surgery or less invasive techniques. As can be readily appreciated by the improved sensitivity of the methods described herein, early detection of a specific level of fibrosis can be beneficial in the development of an effective treatment plan. Previous methods of diagnosis may have resulted in an incorrect determination of the level of fibrosis that may lead to inadequate treatment plans. In accordance with many embodiments, effective treatment plans can be developed and accurately targeted towards the specific level of fibrosis due to the improved sensitivity described herein.

The above discussion focused on various tissue analysis techniques and/or parameters that can be used and/or quantified in the tissue sample analysis. It should be understood that the techniques and/or parameters discussed are not limited to those illustrated herein but can be expanded in accordance with the various embodiments described herein. Furthermore, it should be appreciated that the number and type of parameters quantified are not limited to a specific analysis or image type but can vary from image to image and at various stages of image processing and that they can be used in conjunction or separate. Additionally, the systems and methods discussed below can be used in combination or separately from the above techniques and parameters described in order to analyze, diagnose, and treat the various levels of fibrosis.

Systems and Methods of Analysis

Figure 15:
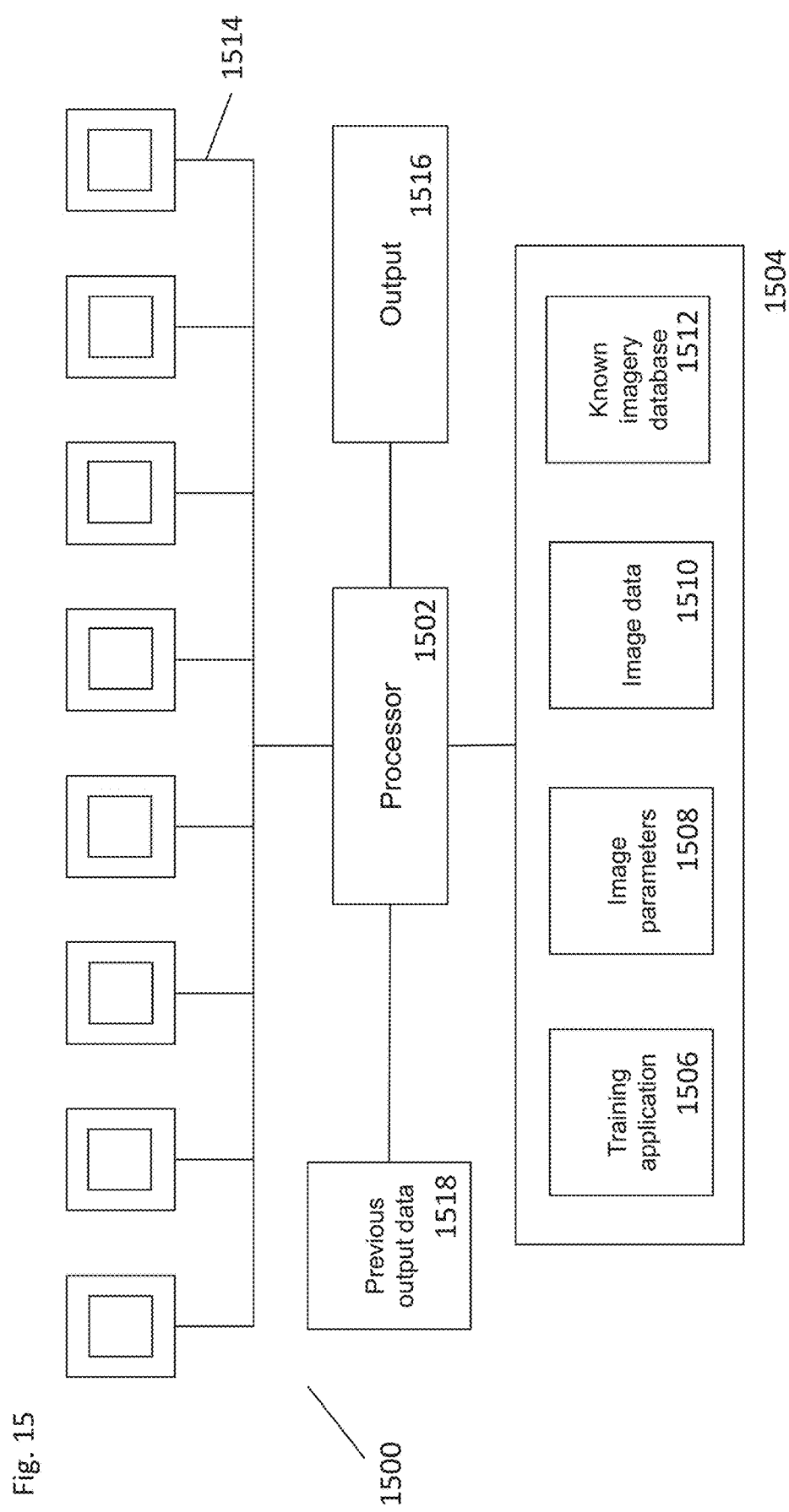
FIG. 15 illustrates a system for processing tissue images for classification in accordance with embodiments of the invention.

Turning now to FIG. 15, many embodiments may be incorporated into a system for analyzing tissue image data utilizing many of the methods described above. For example, some embodiments may consist of an image processing system 1500 that has a processing unit 1502. The processing unit can be connected to a memory system 1504 or some type of database storage system. The memory system 1504 may be configured with a neural network training program 1506 as well as a data base containing the various image parameters 1508 that may be analyzed. Additional embodiments may contain various types of image data 1510 and/or a known imagery database 1512 for use in the analysis of the various input images 1514. It can be appreciated that various embodiments may be capable of receiving a number of different images 1514 from a patient that may contain fibrotic tissue samples as well as normal tissue samples. As illustrated above, many embodiments may be capable of processing, analyzing, and comparing fibrotic images to generate an output 1516 of the type and severity of the fibrotic condition. Additionally, many embodiments may incorporate previous output data 1518 into the system such that any subsequent analysis can be augmented by the most recent datasets.

Figure 16:
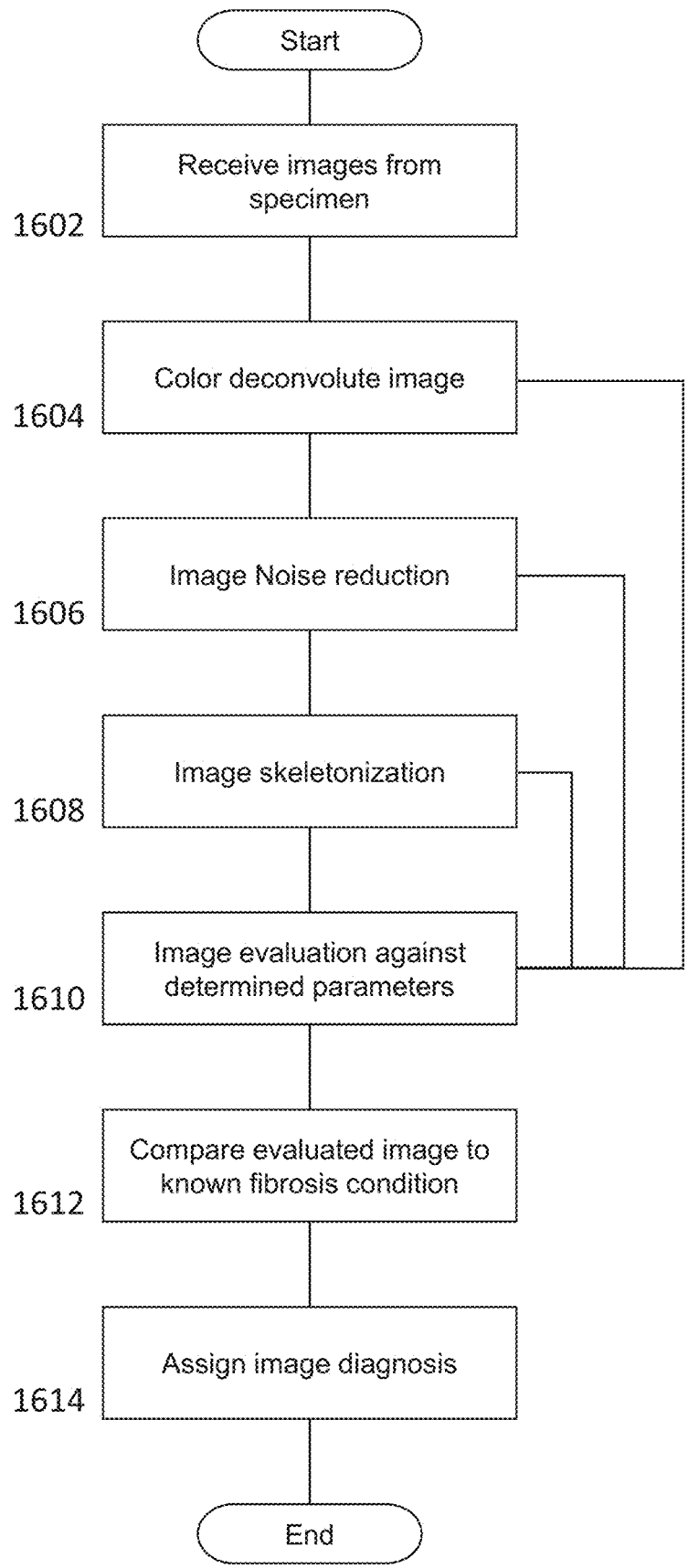
FIG. 16 illustrates a process flow of tissue analysis in accordance with embodiments of the invention.

FIG. 16 illustrates a flow diagram of a method for processing and analyzing input images of various tissue samples. The process can gather or receive (1602) a number of input images of one or more patients. The process can color deconvolute (1604) the input images in various embodiments in order to simplify the image for analysis. The input images can be further processed through a noise reduction (1606) to remove cells and reduce (1608) the image to a skeletonized image. The skeletonized image 1608 can then be analyzed (1610) against a set of weighted parameters and then compared (1612) to a known data set to appropriately determine (1614) the type and severity of the fibrotic condition.

Figure 17B:
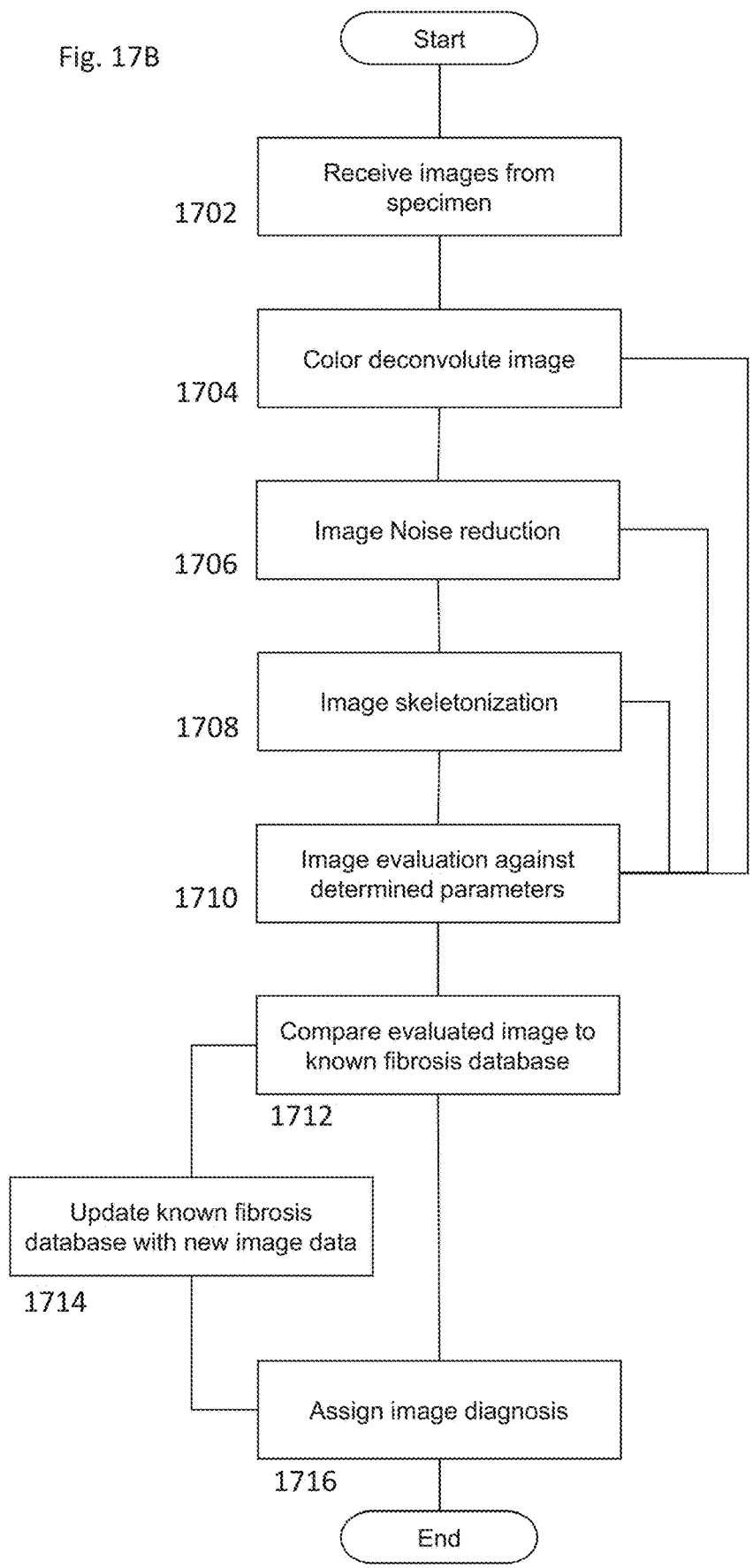

In various other embodiments, processes may involve additional steps or may be processes designed to improve the neural network's sensitivity to input images. For example, FIGS. 17A and 17B illustrate a process that can be enhanced with updated data form analyzed images. The process may receive (1702) input images for processing involving color deconvolution (1704) and noise reduction (1706). The skeletonized images (1708) can then be analyzed (1710) and compared (1712) to the known databases of image for the respective disease. In various embodiments, the new data set can then be used to further train or improve the sensitivity of the overall system and neural network. Subsequently, the continuous an autonomous updating of the neural network can allow for an increased number of parameters to be used which further enhances the system's capability to accurately analyze images for condition and/or severity. FIG. 17A illustrates the continuous updating 1714 of the assigned diagnosis 1716 into the system in order to expand the parameters used to analyze and quantify the respective images.

Figure 18:
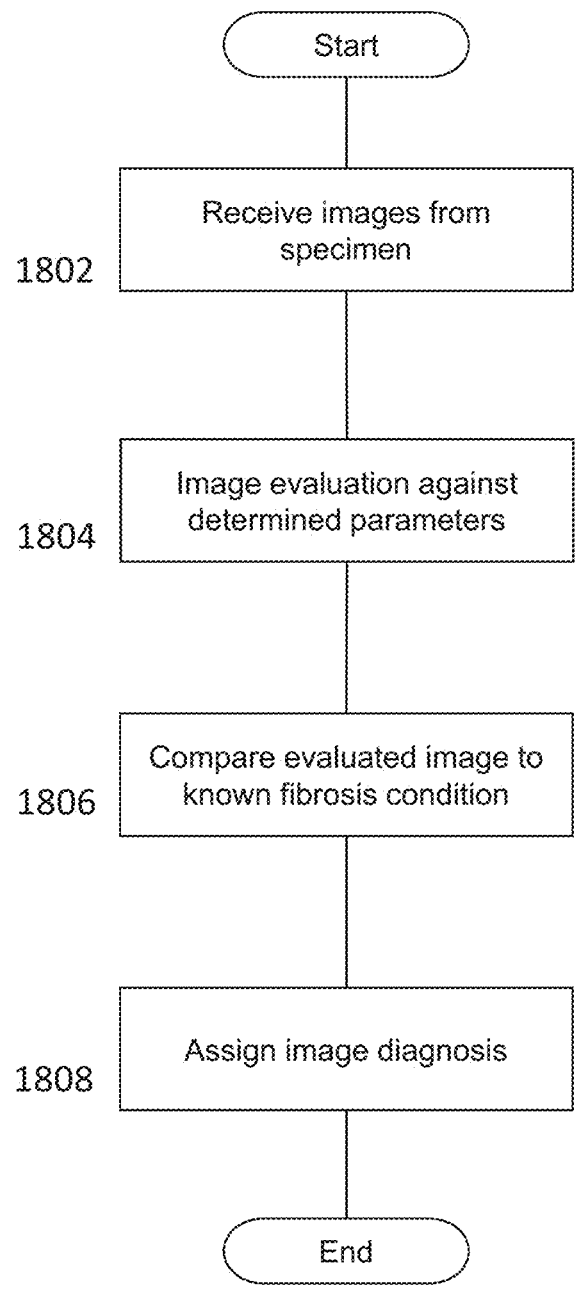
FIG. 18 illustrates a process flow of a tissue analysis in accordance with embodiments of the invention.
Figure 19A:
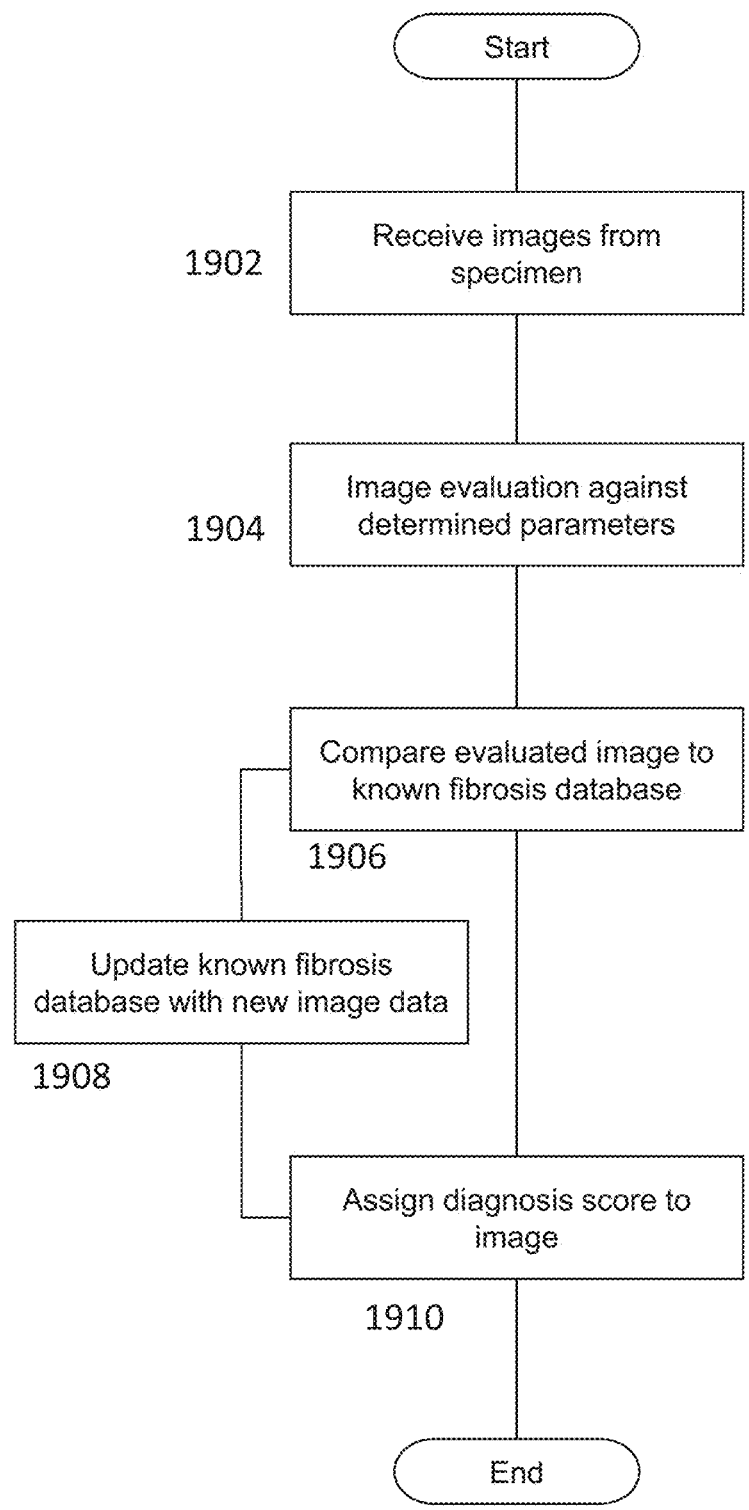
FIGS. 19A and 19B illustrate a process flow for machine learning in accordance with embodiments of the invention.
Figure 19B:
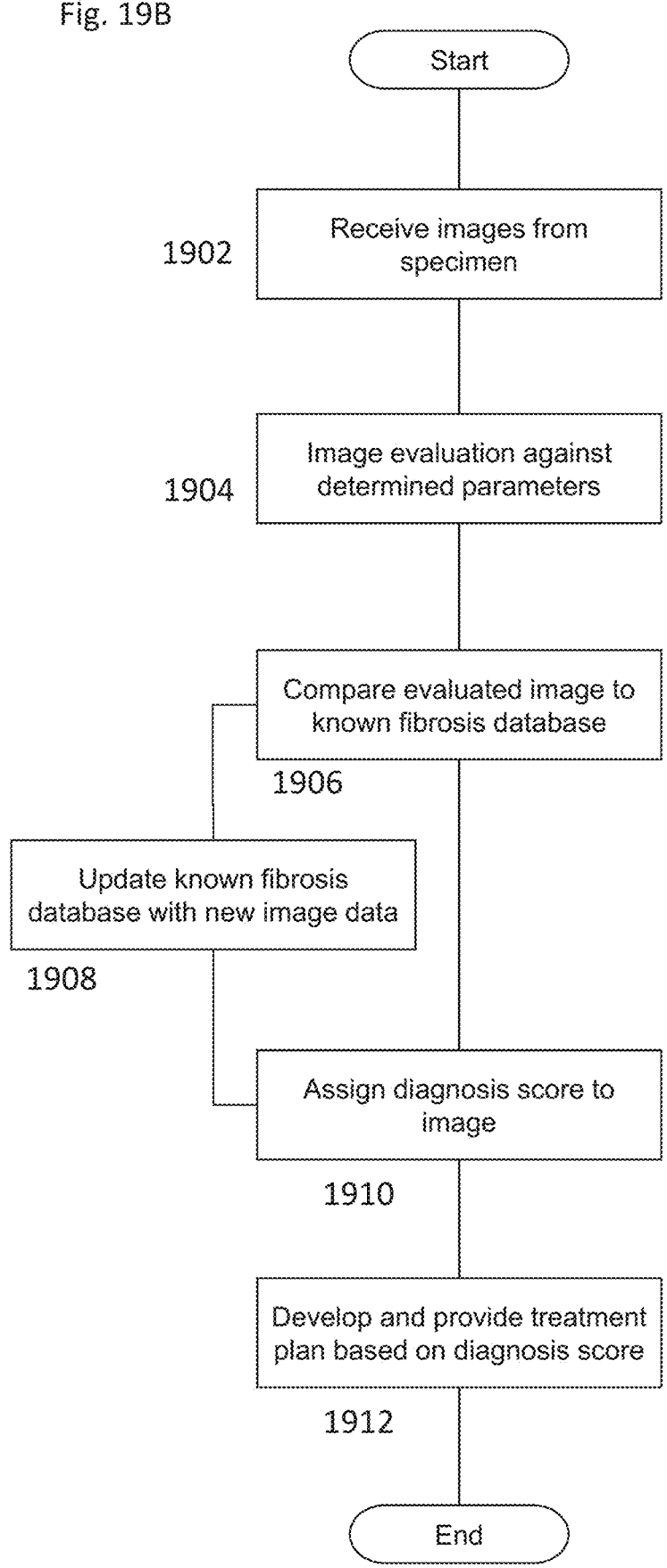

FIGS. 18 through 19B illustrate various embodiments of processes respectively that would be considered unsupervised due the lack of labels placed on the images which can occur through extensive processing. One example of an unsupervised system can be a convolutional neural network, which contains many layers of connected "hidden layer" neurons that effectively define their own image features that can differentiate the different conditions provided to it rather than rely on a set of provided conditions. In numerous embodiments, the process receives (1802) images and evaluates (1804) the images against the set of desired parameters for a given disease. The evaluated images can then be compared (1806) to known datasets for the appropriate classification of disease. Various conditions may not allow for the greater level of image processing as previously discussed processes. Therefore, various embodiments may be adaptable to analyze (1804) less processed images in order to assign or determine (1808) the disease and severity. Accordingly, it can be appreciated that with increased numbers of images and data sets, improved sensitivity of the process 1800 can be achieved. Similarly, as applied to an unsupervised system, the analysis of the images can work to provide an increased number of parameters depending on the depth of the neural network configuration. For example, the process in FIGS. 19A and 19B illustrate an embodiment in which the system or database can be updated with information. In numerous embodiments, the process illustrates a process for analyzing received (1902) images. The received (1902) images can be evaluated (1904) against a set of known parameters and quantified (1906). As the process continues to process image samples, it can be continuously updated 1908 with new parameters as discovered by the system. Subsequently, the analyzed image can be used to assign (1910) a diagnosis score for the image that can be representative of a level of fibrosis. As can be appreciated, additional steps of developing a treatment plan (1912) for the diagnosed condition can be implemented as illustrated in FIG. 19B.

The above discussion focused on the various systems and methods that can be used to effectuate the fibrotic tissue analysis. It should be understood that the systems and methods described herein can be used in combination or separately to perform tissue image processing, analysis, diagnosis, and/or treatment.

Summary & Doctrine of Equivalents

As can be inferred from the above discussion, the above-mentioned concepts can be implemented in a variety of arrangements in accordance with embodiments of the invention. Specifically, systems and methods capable of receiving tissue sample images and analyzing them in order to categorize them into specific disease categories and/or severities that can be used for diagnosis and treatment determinations.

Accordingly, although the present invention has been described in certain specific aspects, many additional modifications and variations would be apparent to those skilled in the art. It is therefore to be understood that the present invention may be practiced otherwise than specifically described. Thus, embodiments of the present invention should be considered in all respects as illustrative and not restrictive.

What is claimed is:

1. A method for tissue analysis comprising:
    obtaining a set of one or more tissue sample images taken of a patient, wherein the set of tissue sample images comprises tissue stained with Masson's Trichrome, Picrosirius Red, or reticulin silver;
    processing, using a computational system, the set of tissue sample images such that a fiber network can be identified and quantified within each tissue sample image, wherein processing comprises performing color deconvolution of the set of tissue sample images, wherein at least one tissue sample image of the set comprises Picrosirius red stain of the tissue, and wherein performing color deconvolution comprises reducing the Picrosirius red stain to red mature fibers and green immature fibers;
    evaluating, using the computational system, the set of processed sample images against a set of parameters wherein the parameters of the set of parameters correspond to fiber characteristics, wherein the parameters of the set of parameters are quantified from the set of processed sample images and wherein the quantified parameters are weighted against a known set of fiber characteristics for establishing a level of fibrosis; and
    assigning, using the computational system, a fibrotic tissue score to the set of tissue sample images that is representative of the level of fibrosis, wherein the fibrotic tissue score is a number within a continuous range.

2. The method of claim 1, wherein the set of tissue sample images comprise a plurality of tissue sample images, wherein the plurality of tissue sample images is representative of a number of different potential diseases.

3. The method of claim 1, wherein the parameters of the set of predetermined parameters are selected from a group consisting of length, width, number of fibers, brightness, persistence, alignment, number of branch points, Euler number, perimeter, solidity, eccentricity, and equivalent diameter.

4. The method of claim 1, wherein the processing step further comprises reducing image noise in at least one image of the set of images.

5. The method of claim 4, wherein the image noise reduction is done by adaptive edge preserving.

6. The method of claim 1, wherein the processing step further comprises performing image binarization of at least one image of the set of images.

7. The method of claim 1, wherein the processing step further comprises performing color deconvolution, noise reduction, and binarization of each image of the set of images.

8. The method of claim 1, wherein the the computational system comprises a neural network system having an input layer, a hidden layer, and an output layer, wherein the evaluating step is completed utilizing the neural network system.

9. The method of claim 8, wherein the neural network system of is an unsupervised neural network.

10. The method of claim 8, wherein the neural network system is a supervised neural network.

11. The method of claim 8, wherein the neural network system has a plurality of hidden layers.

12. The method of claim 8, further comprising producing, using the computational system, a data set of evaluated and assigned images wherein the data set is used for new set of input images.

13. The method of claim 1, further comprising developing a treatment plan for the patient based on the assigned fibrotic tissue score.

14. The method of claim 13, further comprising treating the patient based on the developed treatment plan in accordance with the assigned fibrotic tissue score.

15. The method of claim 1, further comprising updating, using the computational system, a database of tissue parameters with the assigned fibrotic tissue score, wherein a subsequent set of tissue image samples can be analyzed utilizing the updated database of tissue parameters.

16. The method of claim 1, wherein the evaluate step further directs the processor to project the score onto a t-SNE.

17. A computational system for analyzing tissue sample images comprising:
    a processor and a memory, wherein the memory comprises a tissue analysis application that directs the processor to:
        receive a set of one or more tissue sample images taken of a patient, wherein the at least one sample image comprise tissue stained with Masson's Trichrome, Picrosirius Red, reticulin silver,
        process the set of tissue sample images such that a fiber network can be identified and quantified within each tissue sample image, wherein processing comprises performing color deconvolution of the set of tissue sample images, wherein at least one tissue sample image of the set comprises Picrosirius red stain of the tissue, and wherein performing color deconvolution comprises reducing the Picrosirius red stain to red mature fibers and green immature fibers,
        evaluate the set of processed sample images against a set of parameters wherein the parameters of the set of parameters correspond to fiber characteristics, wherein the parameters of the set of parameter are quantified from the set of processed sample images and wherein the quantified parameters are weighted against a known set of fiber characteristics for establishing a level of fibrosis, and
        assign a fibrotic tissue score to the set of tissue sample images that is representative of the level of fibrosis, wherein the fibrotic tissue score is a number within a continuous range.

* * * * *